United States Patent
Yamaya

(10) Patent No.: US 10,973,395 B2
(45) Date of Patent: Apr. 13, 2021

(54) ENDOSCOPE COVER, ENDOSCOPE, COVER UNIT, AND ENDOSCOPE UNIT

(71) Applicant: OLYMPUS CORPORATION, Tokyo (JP)

(72) Inventor: Koji Yamaya, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 375 days.

(21) Appl. No.: 15/950,288

(22) Filed: Apr. 11, 2018

(65) Prior Publication Data

US 2018/0228348 A1 Aug. 16, 2018

Related U.S. Application Data

(63) Continuation of application No. PCT/JP2017/000670, filed on Jan. 11, 2017.

(30) Foreign Application Priority Data

Jan. 14, 2016 (JP) .............................. JP2016-005542

(51) Int. Cl.
*A61B 1/00* (2006.01)
*A61B 1/018* (2006.01)
(Continued)

(52) U.S. Cl.
CPC ........ *A61B 1/00135* (2013.01); *A61B 1/0014* (2013.01); *A61B 1/00089* (2013.01);
(Continued)

(58) Field of Classification Search
CPC ............ A61B 1/00135; A61B 1/00089; A61B 1/00091; A61B 1/00098; A61B 1/0014; A61B 1/018; A61B 1/0676; G02B 23/24
See application file for complete search history.

(56) References Cited

U.S. PATENT DOCUMENTS 5,730,701 A * 3/1998 Furukawa ............ A61B 1/0008
600/121
5,860,913 A * 1/1999 Yamaya ............. A61B 1/00091
600/121
(Continued)

FOREIGN PATENT DOCUMENTS

JP H10-127578 A 5/1998
JP 2003-102668 A 4/2003
(Continued)

OTHER PUBLICATIONS

International Search Report dated Mar. 21, 2017 issued in PCT/JP2017/000670.
(Continued)

*Primary Examiner* — Timothy J Neal
*Assistant Examiner* — William B Chou
(74) *Attorney, Agent, or Firm* — Scully, Scott, Murphy & Presser, P.C.

(57) ABSTRACT

An endoscope cover attached in a lock state to a protruding lock portion of a distal framing portion of an insertion section of an endoscope, includes: a cover main body including an annular portion and which is attached to the distal framing portion along a longitudinal axis; a depressed lock portion provided on the cover main body and locked to the protruding lock portion of the distal framing portion; and a groove provided on a part including the proximal end of the annular portion and in which the protruding lock portion is configured to be located when the cover main body is turned with respect to the distal framing portion in the peripheral direction of the longitudinal axis and the protruding lock portion is unlocked from the depressed lock portion.

14 Claims, 33 Drawing Sheets

(51) Int. Cl.
  *G02B 23/24* (2006.01)
  *A61B 1/06* (2006.01)
(52) U.S. Cl.
  CPC ...... *A61B 1/00091* (2013.01); *A61B 1/00098* (2013.01); *A61B 1/018* (2013.01); *A61B 1/0676* (2013.01); *G02B 23/24* (2013.01)

(56) References Cited

U.S. PATENT DOCUMENTS

| | | | |
|---|---|---|---|
| 2007/0246506 A1 | 10/2007 | Hamazaki et al. | |
| 2017/0000316 A1* | 1/2017 | Sueyasu | A61B 1/00066 |
| 2017/0000317 A1* | 1/2017 | Iizuka | A61B 1/00 |
| 2017/0000319 A1* | 1/2017 | Iizuka | A61B 1/00137 |
| 2018/0055344 A1* | 3/2018 | Ando | A61B 1/0011 |
| 2018/0228348 A1* | 8/2018 | Yamaya | G02B 23/24 |

FOREIGN PATENT DOCUMENTS

| | | |
|---|---|---|
| JP | 2007-289434 A | 11/2007 |
| JP | 2014-068676 A | 4/2014 |

OTHER PUBLICATIONS

English translation of International Preliminary Report on Patentability dated Jul. 26, 2018 together with the Written Opinion received in related International Application No. PCT/JP2017/000670.

* cited by examiner

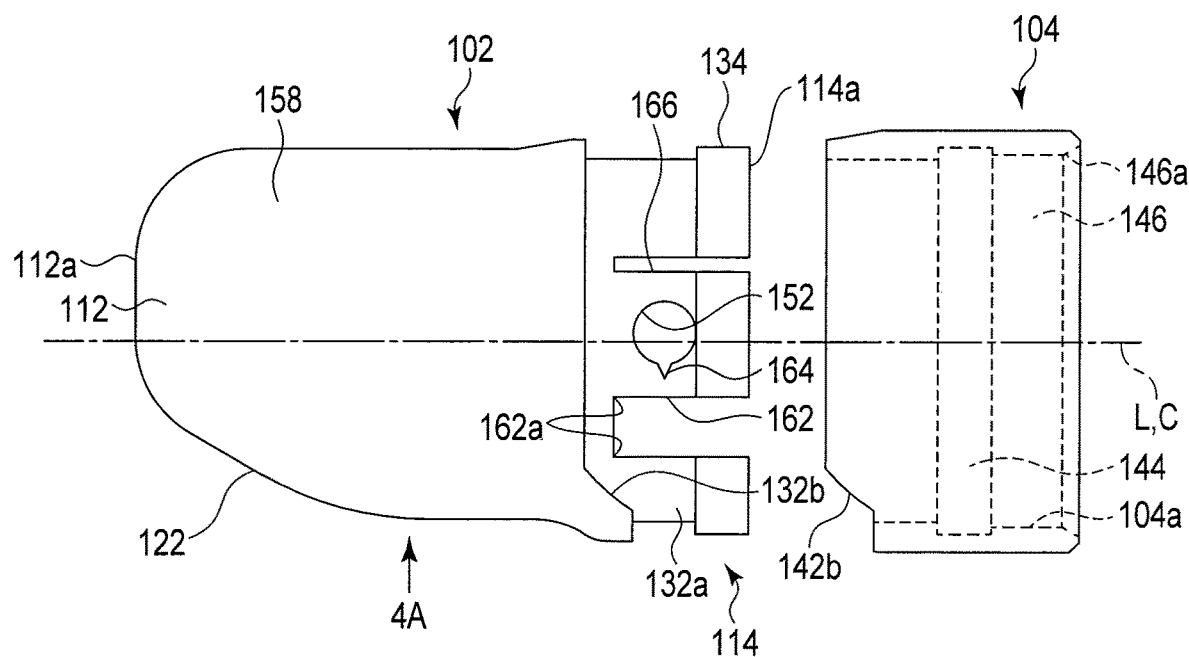
F I G. 4C
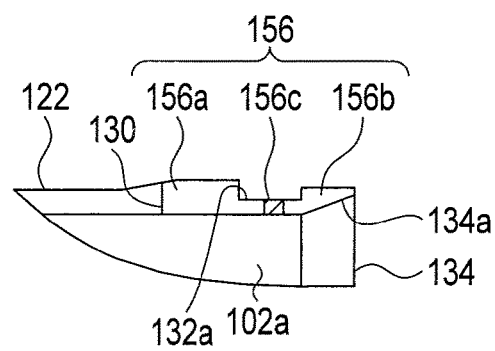
F I G. 4D

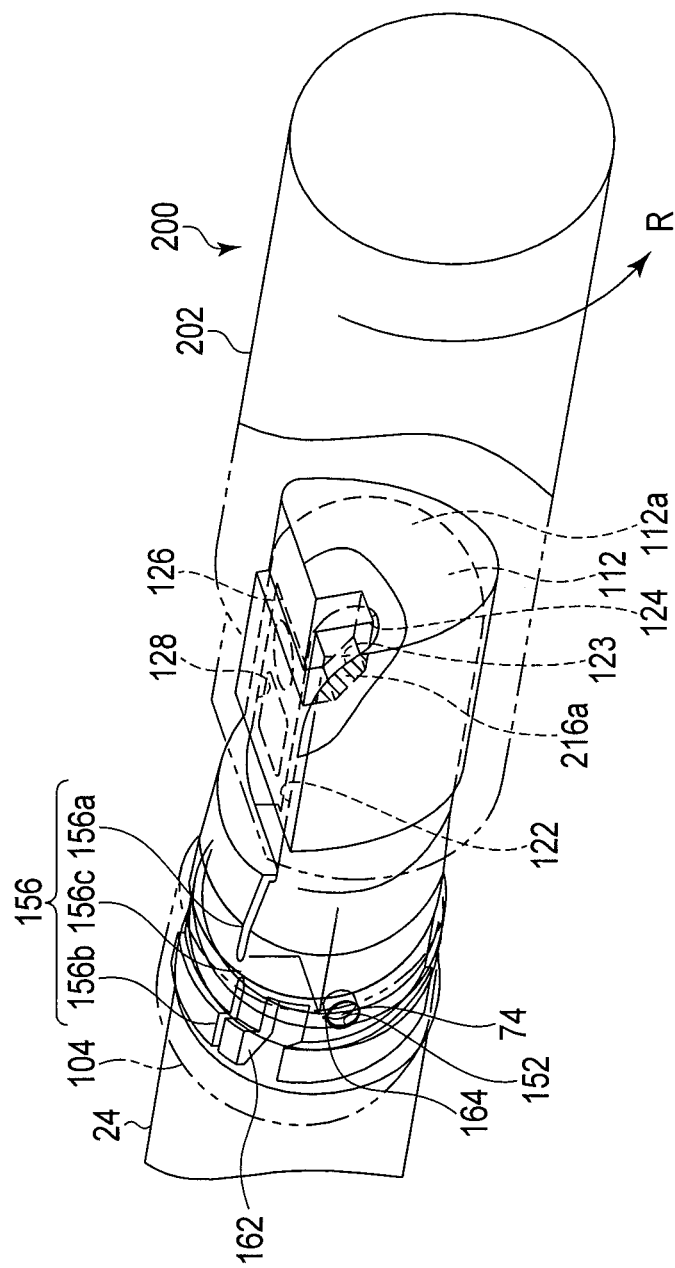
F I G. 12B

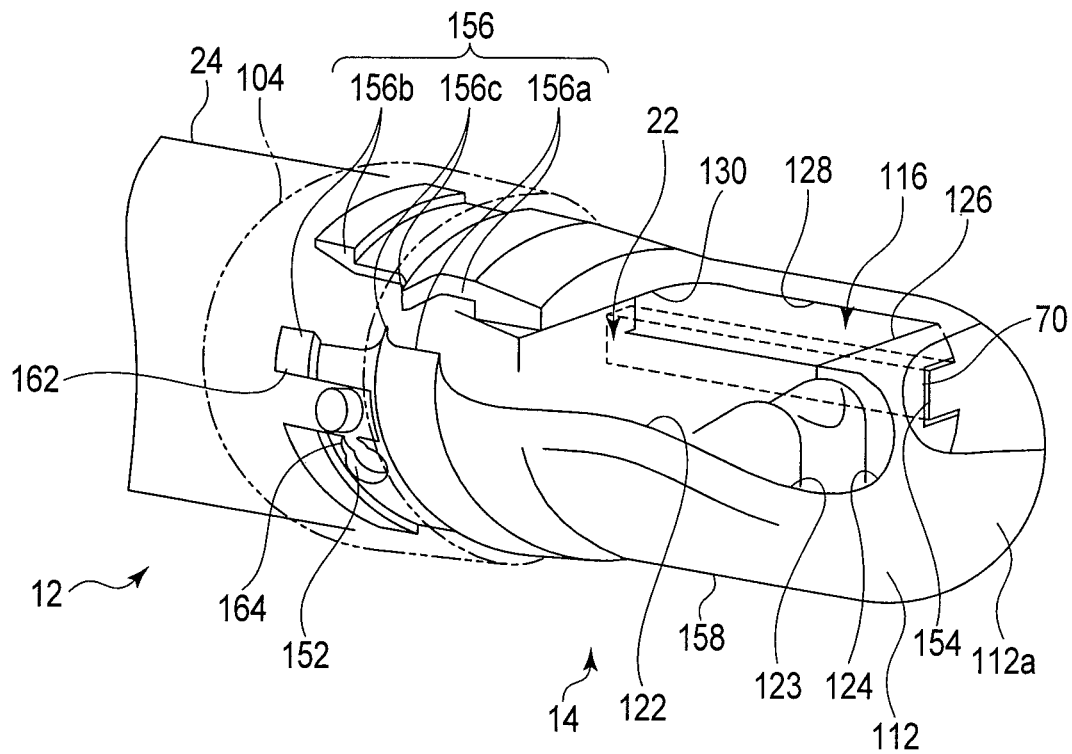
F I G. 14A
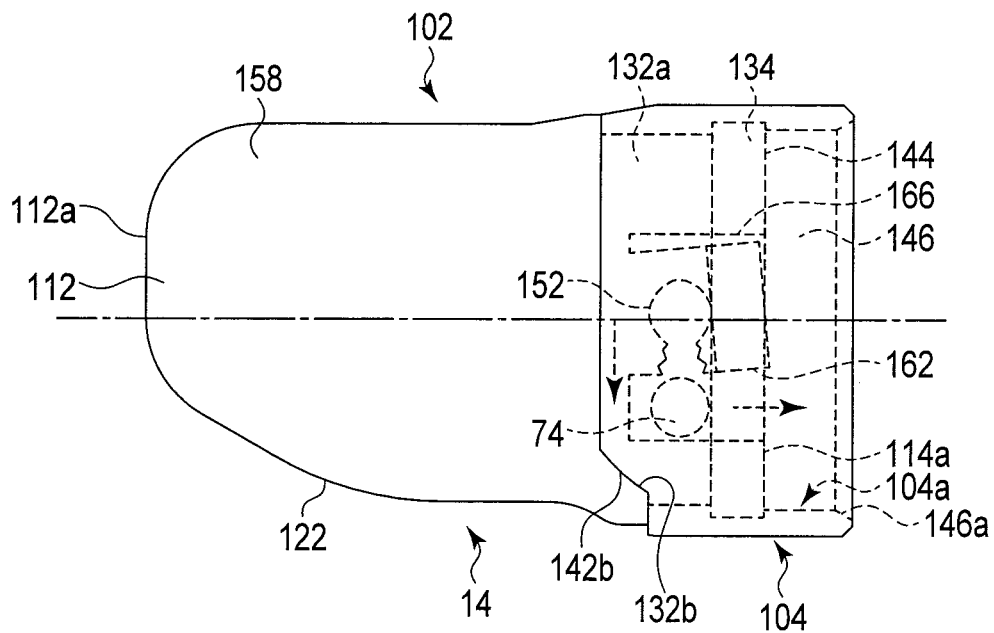
F I G. 14B

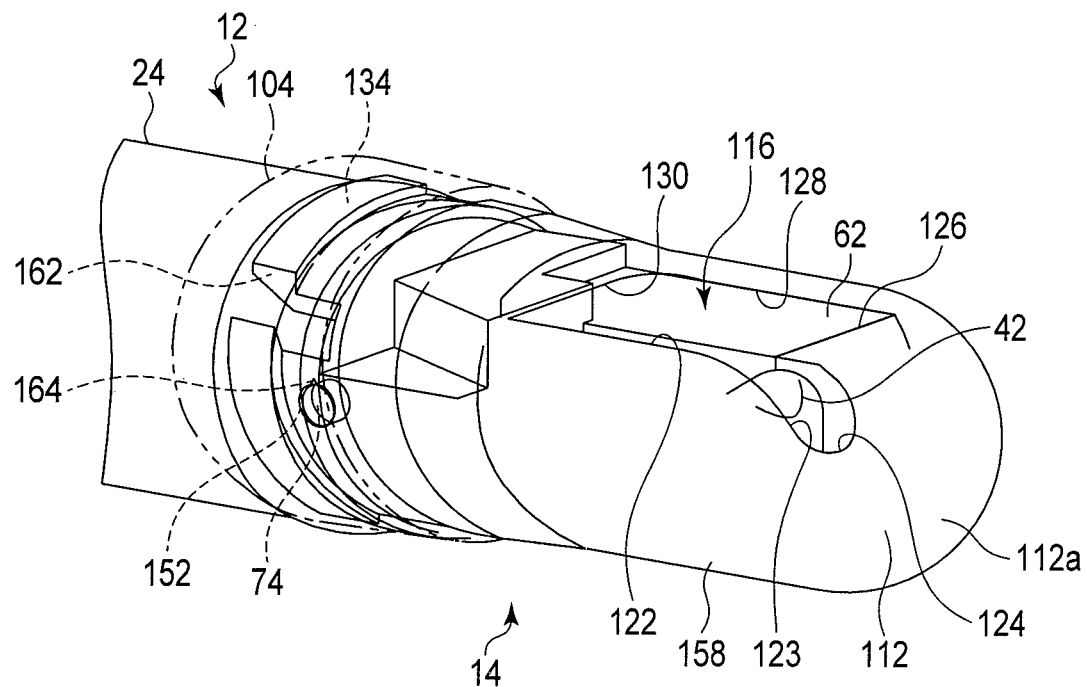
F I G. 23A
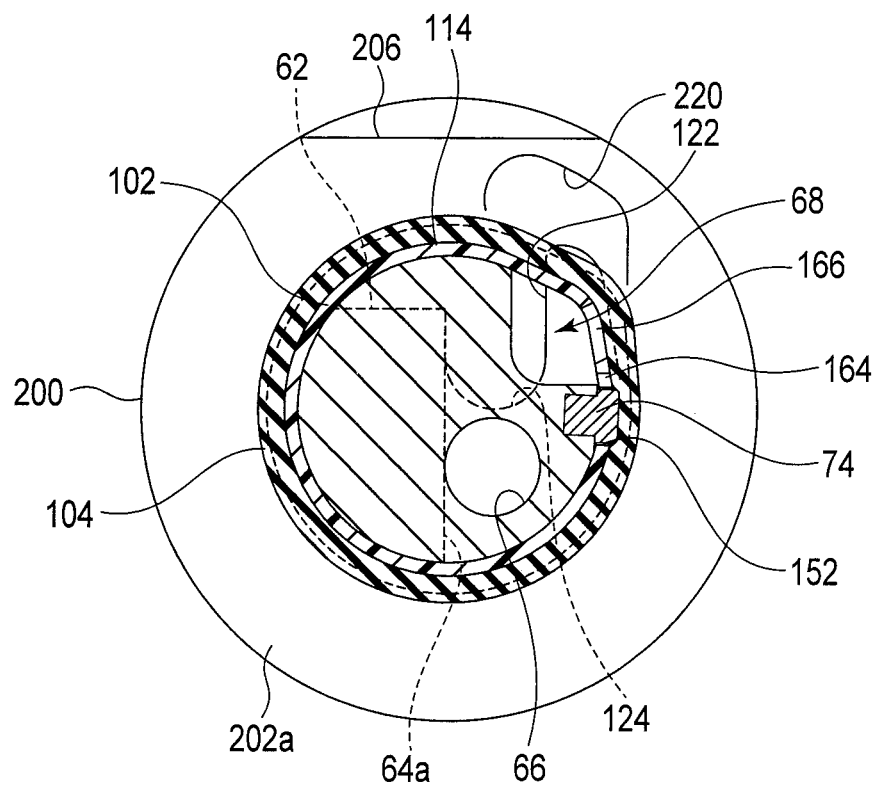
F I G. 23B

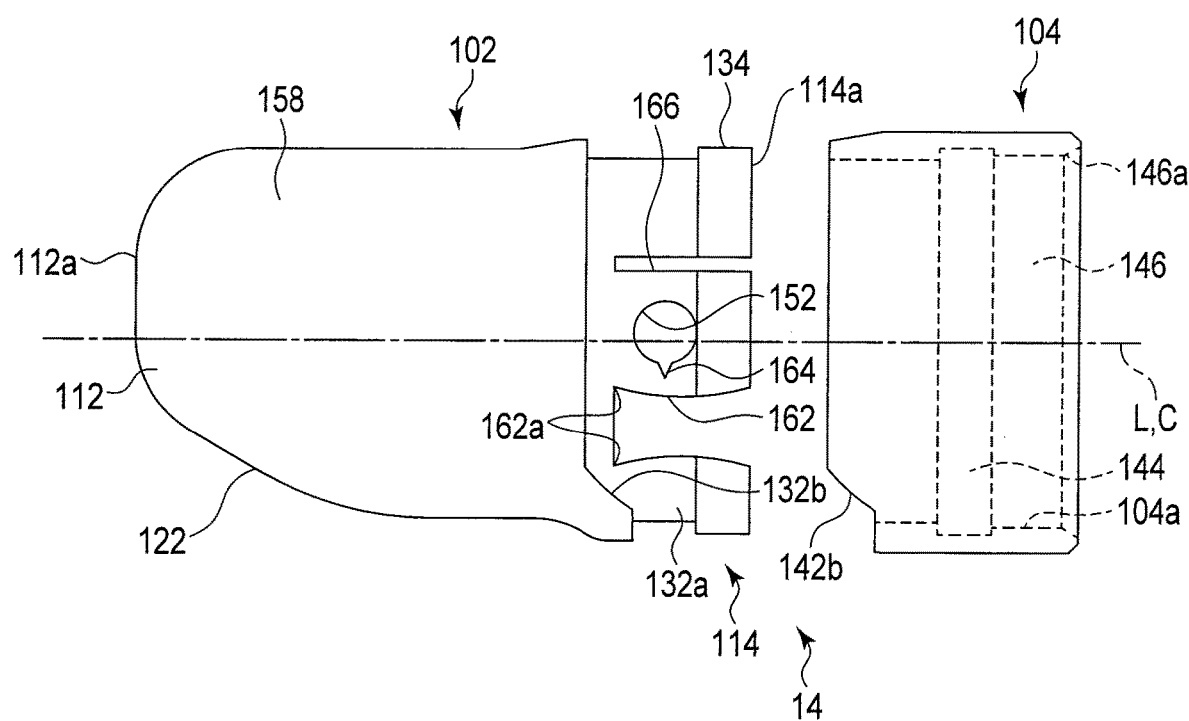
F I G. 25

ENDOSCOPE COVER, ENDOSCOPE, COVER UNIT, AND ENDOSCOPE UNIT

CROSS-REFERENCE TO RELATED APPLICATIONS

This application is a Continuation Application of PCT Application No. PCT/JP2017/000670, filed Jan. 11, 2017 and based upon and claiming the benefit of priority from prior Japanese Patent Application No. 2016005542, filed Jan. 14, 2016, the entire contents of all of which are incorporated herein by reference.

BACKGROUND OF THE INVENTION

1. Field of the Invention

This invention relates to an endoscope cover which is attached to a distal framing portion of an insertion section of an endoscope, an endoscope, a cover unit, and an endoscope unit which each includes the endoscope cover.

2. Description of the Related Art

For example, Jpn. Pat. Appln. KOKAI Publication No. 2003-102668 discloses a cover which is attached to a distal framing portion of an insertion section of an endoscope. This cover is torn along a groove formed from an edge at its proximal end toward a distal side and then detached. When the cover is detached from the distal framing portion, the work of tearing the cover from the edge at its proximal end toward the distal side is done with a tool or fingers.

BRIEF SUMMARY OF THE INVENTION

According to one aspect of the present invention, an endoscope cover which is attached in a lock state to a protruding lock portion of a distal framing portion of an insertion section of an endoscope, includes: a cylindrical cover main body which includes an annular portion and which is attached to the distal framing portion along a longitudinal axis of the insertion section; a depressed lock portion which is provided on the cover main body and which is locked to the protruding lock portion of the distal framing portion; and a groove which is provided on a part including the proximal end of the annular portion of the cover main body along the longitudinal axis and which is provided adjacent to the depressed lock portion in a peripheral direction of the longitudinal axis and in which the protruding lock portion is configured to be located when the cover main body is turned with respect to the distal framing portion in the peripheral direction of the longitudinal axis and then the protruding lock portion is unlocked from the depressed lock portion.

Advantages of the invention will be set forth in the description which follows, and in part will be obvious from the description, or may be learned by practice of the invention Advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 4C is a view of a state seen from an arrow 4C side in FIG. 4A where the endoscope cover which is attached to the distal framing portion of the endoscope according to the first embodiment is exploded;

FIG. 4D is a schematic longitudinal sectional view of the endoscope cover which is attached to the distal framing portion of the endoscope according to the first embodiment, taken along the line 4D-4D in FIG. 4A;

FIG. 12B is a schematic perspective view showing a state where the jig is fitted to the cover to detach the endoscope cover attached to the distal framing portion of the endoscope according to the first embodiment;

FIG. 14A is a schematic perspective view showing a state where the cover is twisted with respect to the distal framing portion, the coupling portion of the fragile portion of the cover and a second fragile portion are broken, and a lock pin of the distal framing portion is disposed in a groove of the cover, to detach the endoscope cover attached to the distal framing portion of the endoscope according to the first embodiment;

FIG. 14B is a schematic view showing a state where the second fragile portion of the cover is broken, the covers moved to a distal side with respect to the distal framing portion along a longitudinal axis from the state where the lock pin of the distal framing portion is disposed in the groove of the cover, and the lock pin, that is, the distal framing portion is pulled out along the groove, to detach the endoscope cover attached to the distal framing portion of the endoscope according to the first embodiment;

FIG. 23A is a schematic perspective view showing a state where the endoscope cover is attached to the distal framing portion of the endoscope according to the second embodiment;

FIG. 23B is a schematic cross sectional view taken along the line 13C-13C in FIG. 13A, showing a state where the jig is fitted to the cover to detach the endoscope cover attached to the distal framing portion of the endoscope according to the second embodiment;

FIG. 25 is a view of a state seen from an arrow 21B side in FIG. 21A where the endoscope cover which is attached to the distal framing portion of the endoscope according to a modification (first modification) of the second embodiment is exploded;

DETAILED DESCRIPTION OF THE INVENTION

Embodiments of the present invention will be described below with reference to the drawings.

The first embodiment is described with reference to FIG. 1 to FIG. 14B.

Figure 1:
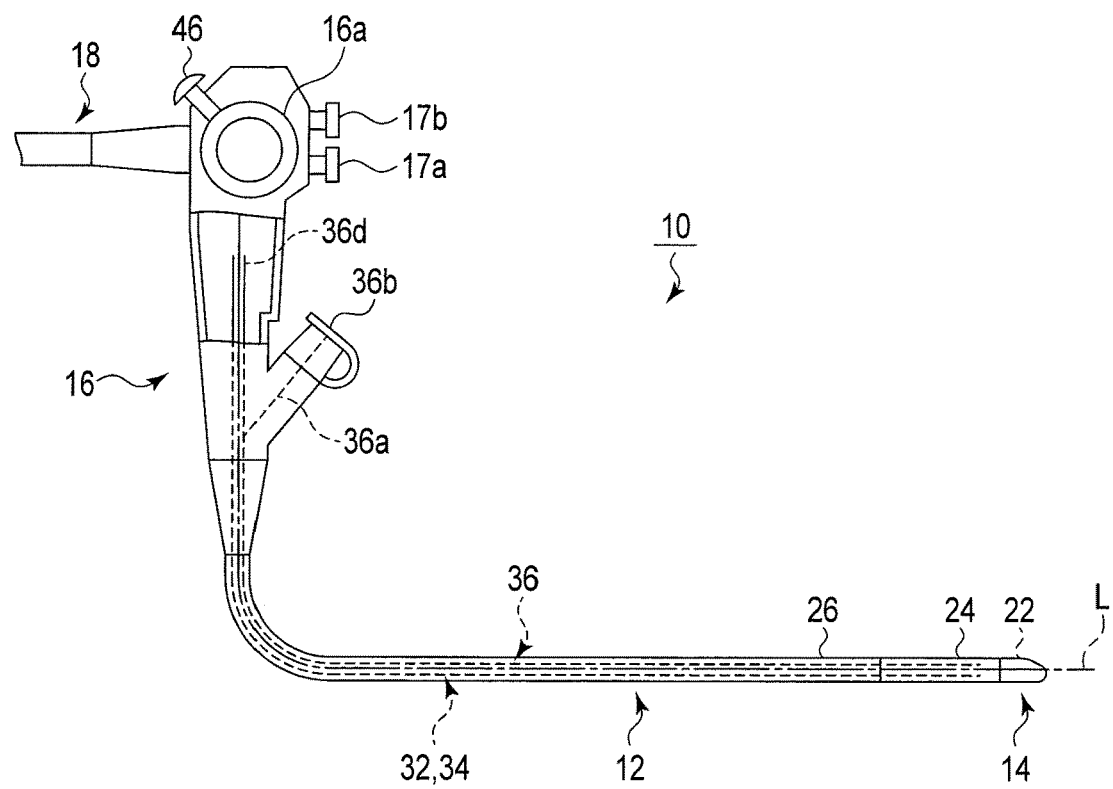
FIG. 1 is a schematic view of an endoscope according to first and second embodiments.
Figure 2A:
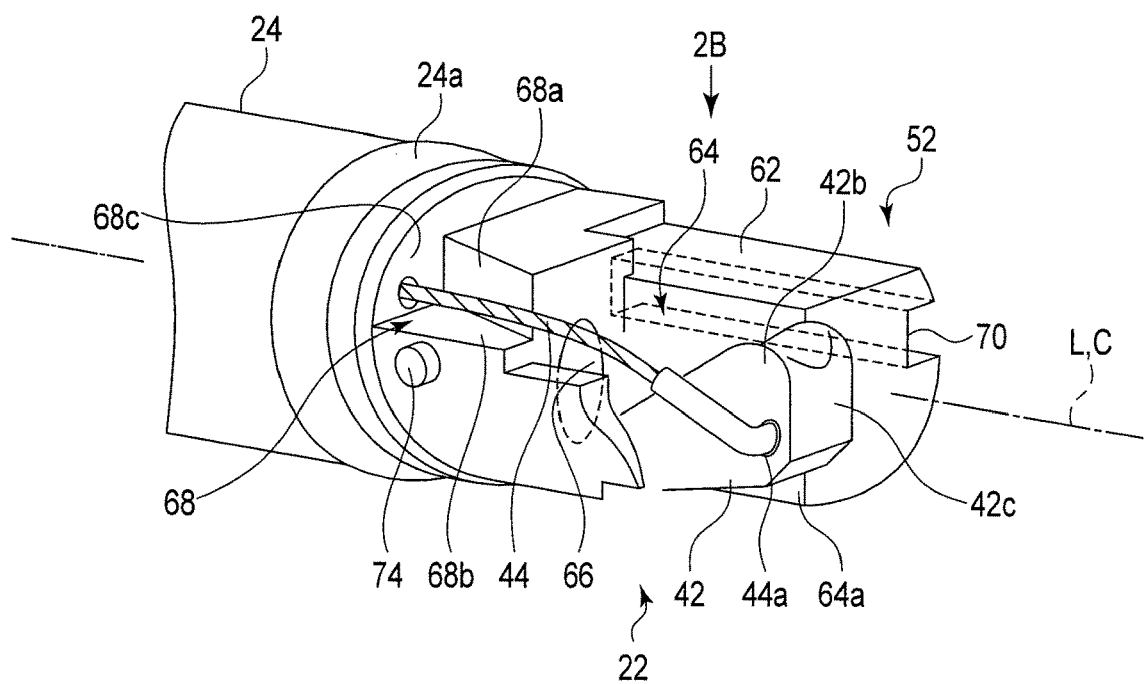
FIG. 2A is a schematic perspective view showing a distal framing portion of the endoscope according to the first embodiment.
Figure 2B:
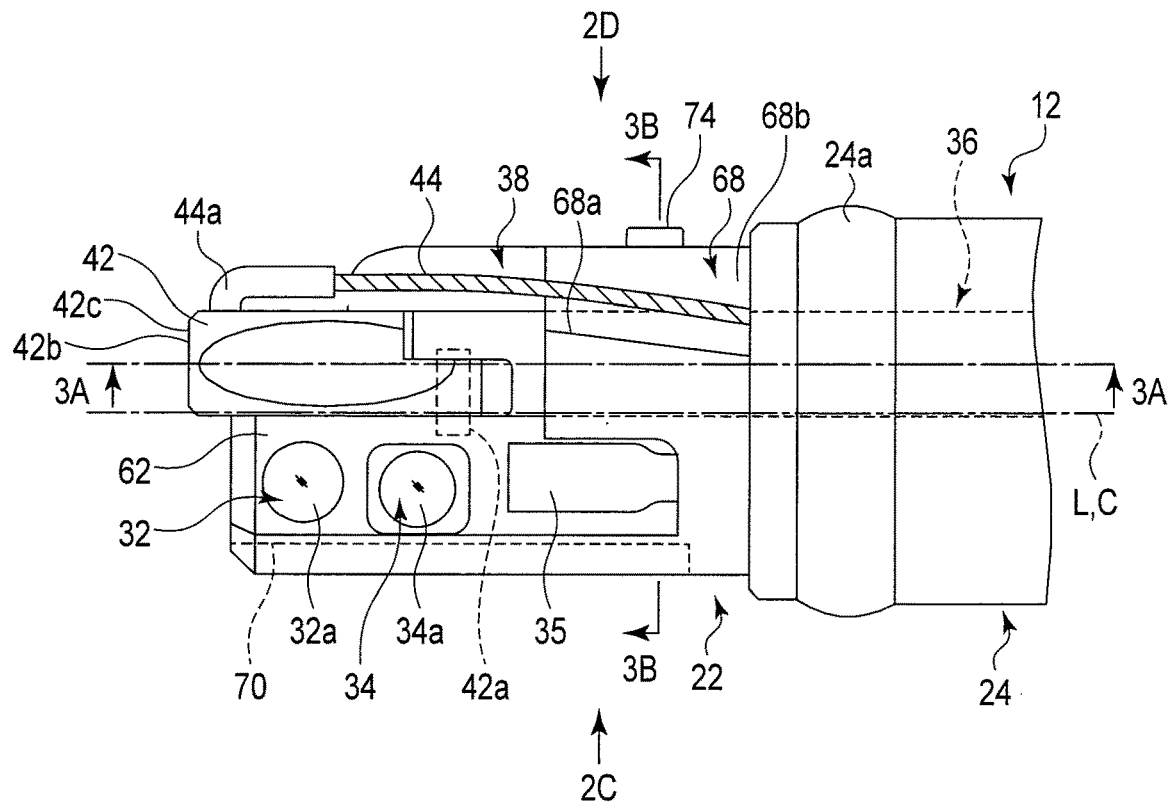
FIG. 2B is a view of the distal framing portion of the endoscope according to the first embodiment seen from an arrow 2B side in FIG. 1A.
Figure 2C:
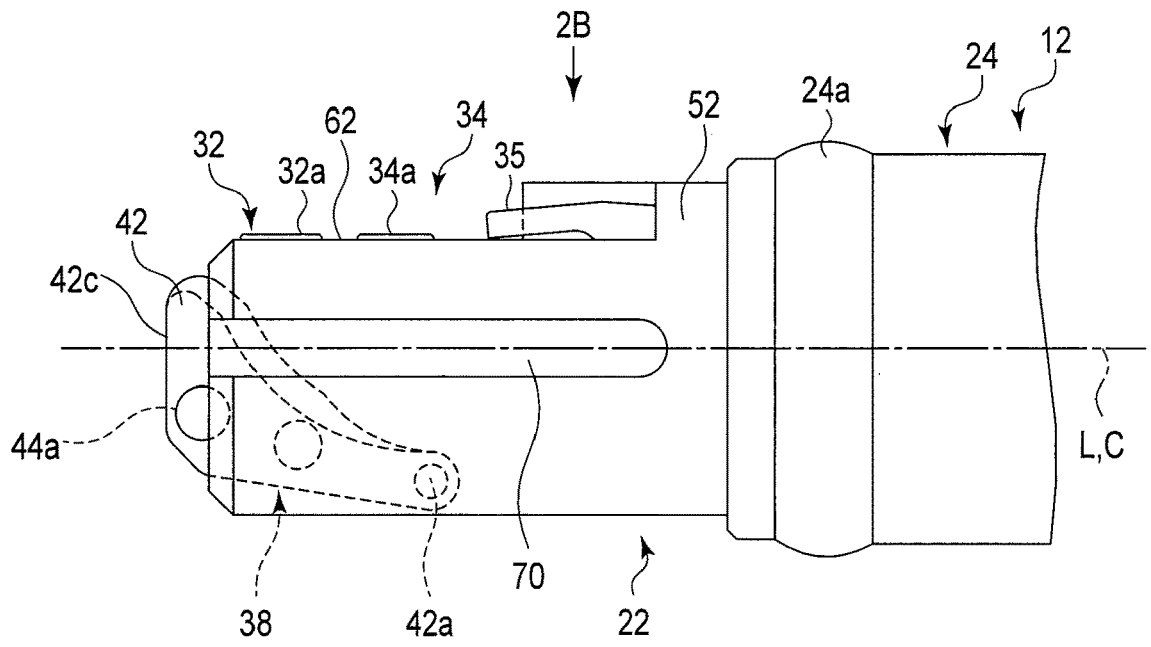
FIG. 2C is a view of the distal framing portion of the endoscope according to the first embodiment seen from an arrow 2C side in FIG. 2B.
Figure 2D:
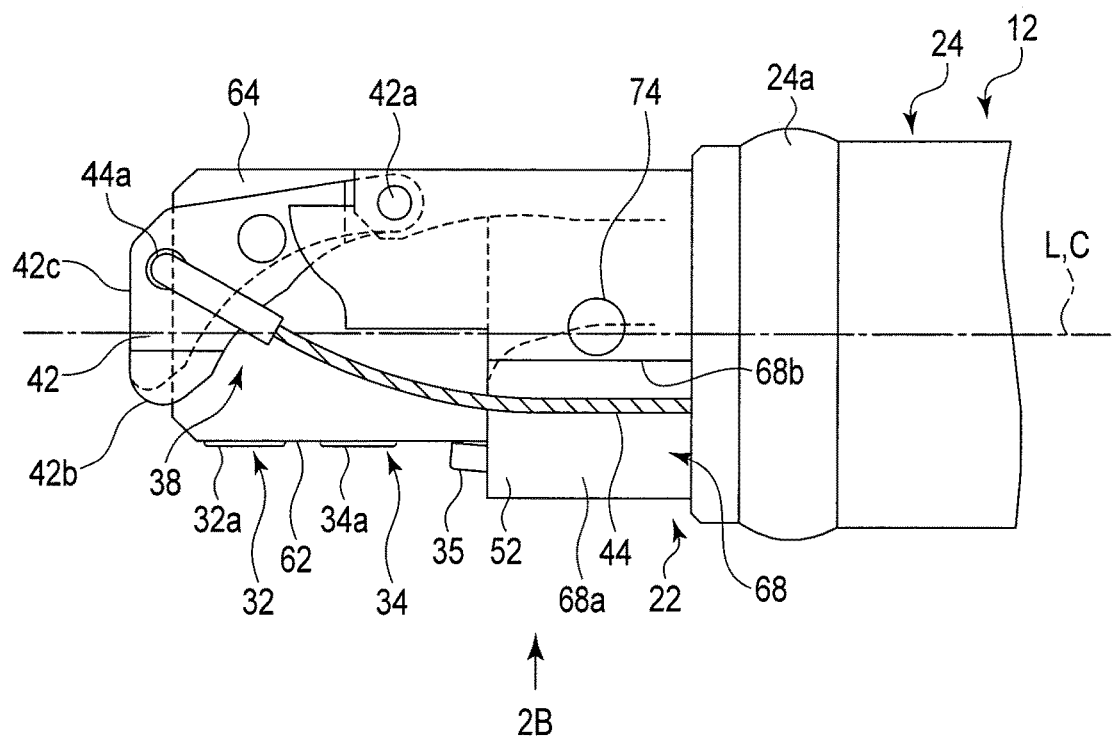
FIG. 2D is a view of the distal framing portion of the endoscope according to the first embodiment seen from an arrow 2D side in FIG. 2B.

As shown in FIG. 1, an endoscope (insertion device) 10 according to the embodiment includes an insertion section 12 which is inserted into a duct such as a lumen, an endoscope cover (hereinafter mainly referred to as a cover) 14 which is attached to a distal end of the insertion section 12 in a fitted state, an operation section 16 which is provided at a proximal end of the insertion section 12 and which is grasped by a user, and a universal cord 18 extending from the operation section 16. Although described in detail later, the cover 14 is formed as a disposable type, and maintains its shape and is thus easily attachable to a distal framing portion 22 of the insertion section 12, but is formed so that it can not be easily detached from the distal framing portion 22 without being at least partly broken.

The insertion section 12 defines a longitudinal axis by the distal end and the proximal end of the insertion section 12. The insertion section 12 includes, in order from its distal end toward its proximal end, the distal framing portion 22, a bending portion 24, and a tubular portion 26. The tubular portion 26 may be a so-called flexible scope having flexibility, or may be a so-called rigid scope which maintains a straight state and is thus resistant to bending. The bending portion 24 can be bent by a publicly known mechanism in response to a knob 16a of the operation section 16 in multiple directions such as two upward and downward directions or four upward, downward, rightward, and leftward directions.

The endoscope 10, which is publicly known and is therefore briefly described, includes an illumination optical system 32, an observation optical system 34, and a treatment instrument insertion channel 36. Additionally, the endoscope 10 includes an air/water supply mechanism and a suction mechanism that are not shown. The air/water supply mechanism includes a later-described nozzle 35 at its distal end, and is operated by a button 17a in the operation section 16. The suction mechanism communicates with the treatment instrument insertion channel 36, and is operated by a button 17b in the operation section 16.

The illumination optical system 32 and the observation optical system 34 are inserted through the distal framing portion 22, the bending portion 24, and the tubular portion 26 of the insertion section 12 of the endoscope 10, the operation section 16, and the universal cord 18. The illumination optical system 32 has an illumination window 32a in the distal framing portion 22. The observation optical system 34 has an observation window 34a in the distal framing portion 22.

The channel 36 has its distal end open in the distal framing portion 22 of the insertion section 12 of the endoscope 10, and has its proximal end open in the vicinity of a proximal portion of the tubular portion 26 of the insertion section 12 or in the operation section 16. Here, as shown in FIG. 1, the opening (not shown) at the proximal end of the channel 36 is in the operation section 16, and a forceps plug 36b is attachable to and detachable from this opening via a pipe sleeve. The channel 36 has a tube 36a whose distal end is fixed to the distal framing portion 22 via a pipe sleeve 36c. In addition, the tube 36a of the treatment instrument insertion channel 36 is branched into, for example, a publicly known suction path 36d inside the operation section 16. The suction path 36d is coupled to the button 17b. A sucked object is discharged from a later-described opening 66 at the distal end of the channel 36 via the pipe sleeve 36c, the tube 36a, the suction path 36d, and the universal cord 18 by a press operation of the button 17b.

In this embodiment, the distal framing portion 22 is formed as a side-viewing type whose observation direction is different from a direction along a longitudinal axis L of the insertion section 12. The endoscope 10 includes a swing mechanism 38 which suitably adjusts, at the distal framing portion 22, the direction of a treatment instrument (not shown) or the like which has passed through the channel 36, and which is able to observe the treatment instrument or the like in a field of view.

The swing mechanism 38, which is publicly known and is therefore briefly described, has its distal end in the distal framing portion 22 of the insertion section 12 of the endoscope 10, and its proximal end in the operation section 16. The swing mechanism 38 includes, in order from the distal end toward the proximal end of the insertion section 12, a swing table 42, a wire 44, and a lever 46. The swing table 42 is supported on the distal framing portion 22 via a support pin 42a. A distal end of the wire 44 is supported on the swing table 42, and a proximal end of the wire 44 is supported on the lever 46. In addition, a publicly known mechanism prevents a liquid or a gas from entering the insertion section 12, specifically, the tubular portion 26 of the insertion section 12 along the wire 44. Preferably, the entry of a liquid or a gas into the operation section 16 of the insertion section 12 and the tubular portion 26 is prevented.

As shown in FIG. 2A to FIG. 3B, the distal framing portion 22 includes a blocked-shaped main body 52. The main body 52 includes a later-described flat portion 62, a storage portion (storage space) 64, the opening 66, a wire moving portion (wire moving space) 68, a guide groove (first guide) 70, and a pin fixing portion 72 which are formed from a circular cylinder of a rigid material such as a stainless steel material. Thus, the main body 52 has a central axis C defined therein. For the simplicity of explanation, the aforementioned longitudinal axis L is described as corresponding to the central axis C.

The main body 52 is provided with the illumination window 32a at the distal end of the illumination optical system 32, the observation window 34a at the distal end of the observation optical system 34, the pipe sleeve 36c in the distal portion of the tube 36a of the channel 36, and the swing table 42 in the distal portion of the swing mechanism 38. Thus, the distal framing portion 22 is formed by the main body 52, the illumination window 32a of the illumination optical system 32, the observation window 34a of the observation optical system 34, the pipe sleeve 36c in the distal portion of the tube 36a of the treatment instrument insertion channel 36, and the swing table 42 and the wire 44 in the distal portion of the swing mechanism 38.

Figure 3A:
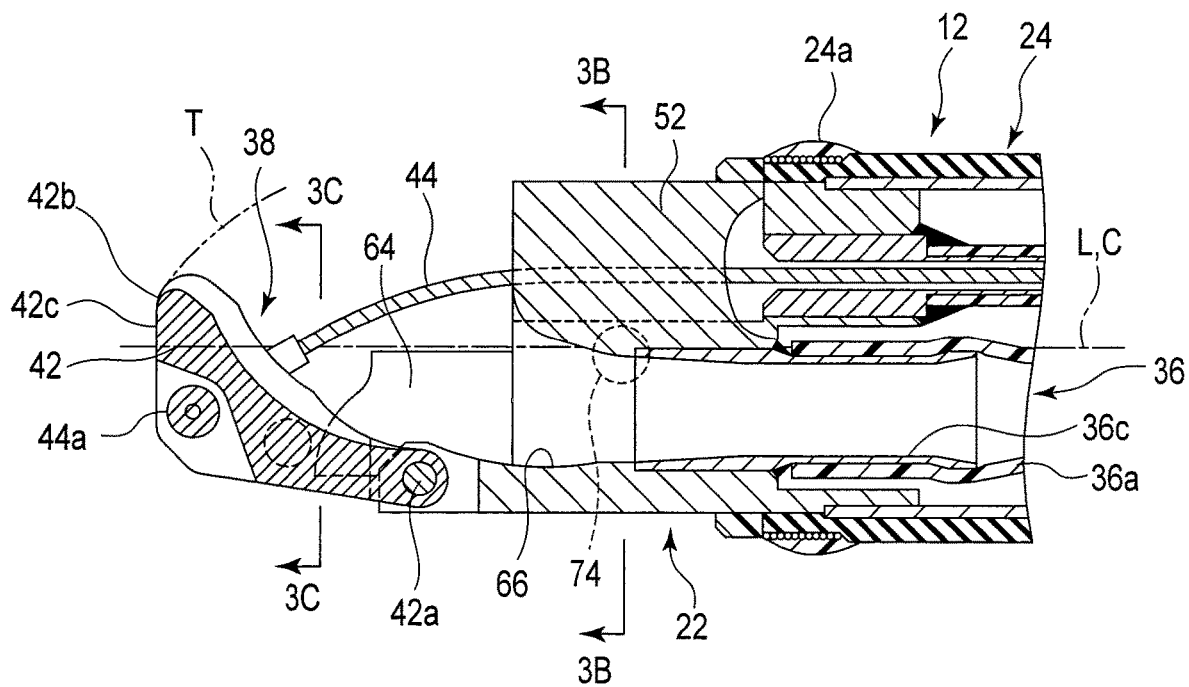
FIG. 3A is a schematic longitudinal sectional view of the distal framing portion of the endoscope according to the first embodiment, taken along the line 3A-3A in FIG. 2B.

The main body 52 includes the flat portion 62 to which the illumination window 32a and the observation window 34a are fixed, the storage portion 64 which swingably stores the swing table 42, and the opening 66 which communicates with the storage portion 64 and also communicates with the channel 36 to guide the treatment instrument to the swing table 42. As shown in FIG. 3A, the distal end of the tube 36a of the channel 36 is fixed to the opening 66. The distal side of the storage portion 64 along the longitudinal axis L, that is, the distal end of the main body 52 is preferably open. In addition, the wire moving portion 68 which moves the wire 44 is formed continuously with the storage portion 64 on the proximal side of the storage portion 64. The wire moving portion 68 is formed on the upper side of the opening 66 in FIG. 3B. The wire moving portion 68 is located adjacent to the flat portion 62 of the main body 52, and formed by walls 68a, 68b, and 68c (see FIG. 2A) which guide the wire 44. It is appropriate that a closed space be formed between the walls 68a, 68b, and 68c of the wire moving portion 68 and the cover 14.

The flat portion 62 of the main body 52 is supposed to be parallel to the longitudinal axis L. That is, here, for the simplicity of explanation, a normal N to the flat portion 62 is formed to be in a direction substantially orthogonal to the longitudinal axis L. The normal N preferably corresponds to the upper side which is one of the curving directions of the bending portion 24. In this way, the upper side of the insertion section 12 is decided, and the lower side, right side, and the left side are decided accordingly. In the flat portion 62 of the main body 52, the illumination window 32a is arranged on the distal side, and the observation window 34a is arranged on the proximal side adjacent to the illumination window 32a. The nozzle 35 is provided on the proximal side of the observation window 34a. The nozzle 35 is directed to the observation window 34a and the illumination window 32a. The nozzle 35 is capable of discharging a liquid such as physiological saline toward the observation window 34a and the illumination window 32a, and also capable of blowing off attached matter on the observation window 34a and the illumination window 32a by air supply.

The storage portion 64 is arranged in a direction orthogonal to the longitudinal axis L in comparison with the flat portion 62. The storage portion 64 forms a space in which the swing table 42 can turn in a predetermined range. The swing table 42 is swingably supported on the main body 52 by the support pin 42a. In addition, in a state where the swing table 42 is disposed at a position (fall position) shown in FIG. 2A to FIG. 3A, a distal face 42c including a distal end portion 42b of the swing table 42 protrudes more on the proximal side than the distal end of the main body 52 along the longitudinal axis L.

A distal end 44a of the wire 44 of the swing mechanism 38 is supported on the swing table 42. In addition, the proximal end (not shown) of the wire 44 of the swing mechanism 38 is supported on the lever 46 of the operation section 16. Because the length of the wire 44 is adjusted, the swing table 42 is disposed at the position (fall position) shown in FIG. 2A to FIG. 3A when the lever 46 is at a first position (pushed up to the maximum), and as the lever 46 is pushed down, the wire 44 is pulled, and the distal end portion 42b of the swing table 42 distal to the support pin 42a swings on the support pin 42a along a virtual line T shown in FIG. 3A. Moreover, the lever 46 is pushed down to the maximum at a second position. At this point, the swing table 42 is disposed at a rise position where the swing table 42 rises to the maximum.

As shown in FIG. 2A to 2C, FIG. 3B, and FIG. 3C, the main body 52 of the distal framing portion 22 includes, on its outer peripheral surface, the guide groove (first restriction portion) 70 as a first guide along the longitudinal axis L. The guide groove 70 is adjacent to the flat portion 62, but is formed at a position away from the storage portion 64, that is, the wire 44 and the swing table 42 of the swing mechanism 38. It is appropriate that the guide groove 70 be continuously formed from the distal end to proximal end of the main body 52.

The pin fixing portion 72 formed on the outer peripheral surface of the main body 52 of the distal framing portion 22. The pin fixing portion 72 is preferably formed adjacent to the wire moving portion 68 and substantially on the side opposite to the guide groove 70 across the central axis C of the main body 52 of the distal framing portion 22. A lock pin (protruding lock portion) 74 protruding in the direction orthogonal to the central axis C is fixed to the pin fixing portion 72.

Figure 3B:
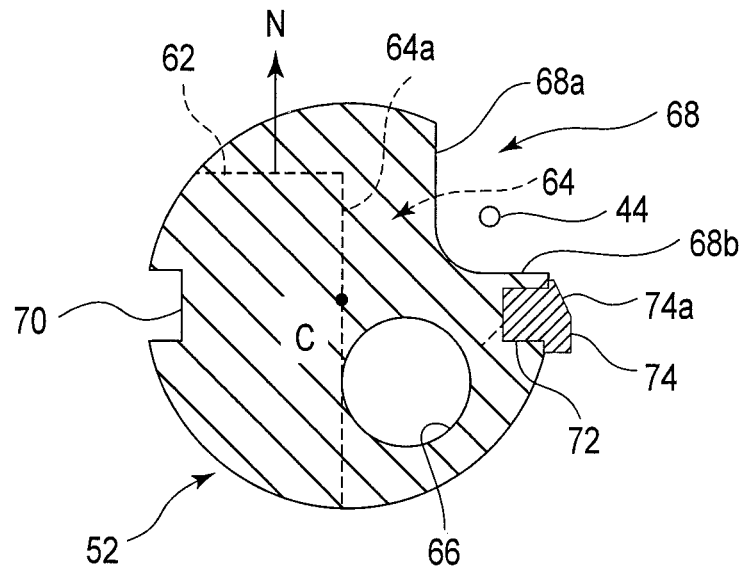
FIG. 3B is a schematic cross sectional view of the distal framing portion of the endoscope according to the first embodiment, taken along the line 3B-3B in FIG. 3A.
Figure 3C:
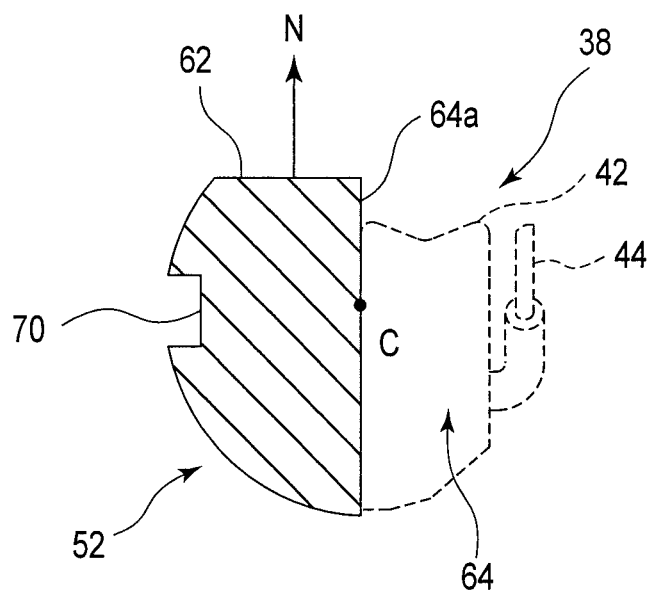
FIG. 3C is a schematic cross sectional view of the distal framing portion of the endoscope according to the first embodiment, taken along the line 3C-3C in FIG. 3A.

When a wall surface 64a of the storage portion 64 shown in FIG. 3B and FIG. 3C is a base level, the right side where the swing mechanism 38 is provided is a first region, and the left side including the flat portion 62 where the illumination optical system 32 and the observation optical system 34 are provided is a second region. At this point, the lock pin 74 located in the first region, and the guide groove (first restriction portion) 70 is located in the second region apart from the lock pin 74.

Next, the disposable type endoscope cover 14 which is attached to the distal framing portion 22 is described with reference to FIG. 4A to FIG. 5D.

Figure 4A:
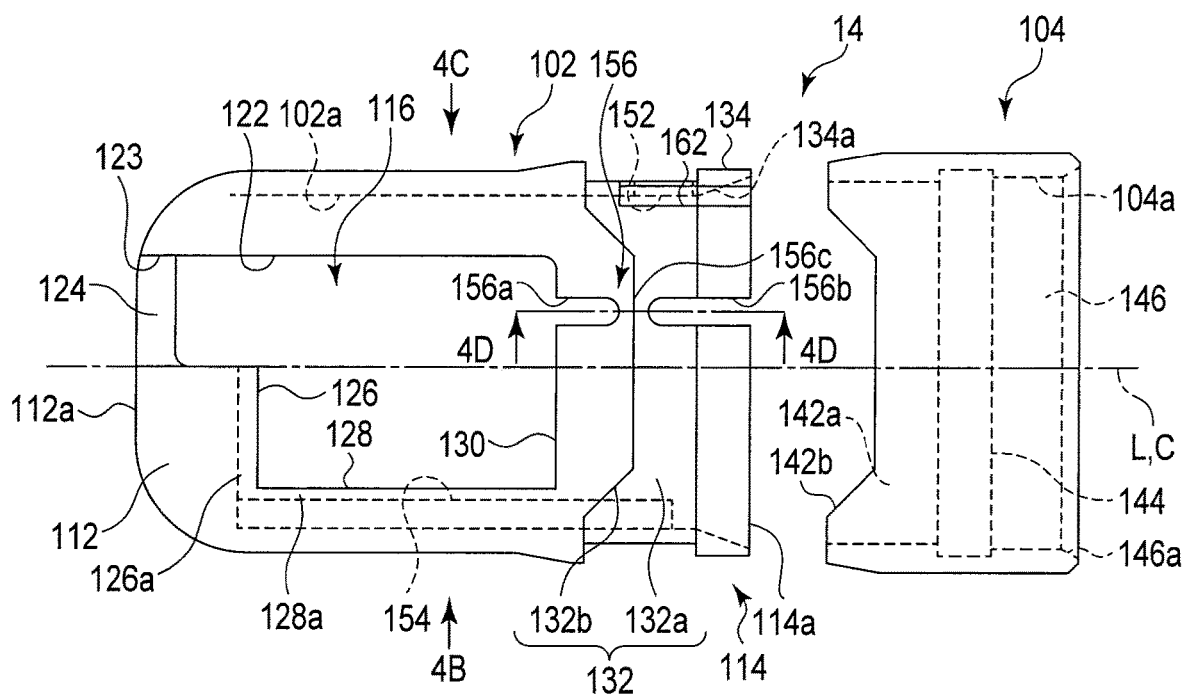
FIG. 4A is a schematic view showing a state where an endoscope cover which is attached to the distal framing portion of the endoscope according to the first embodiment is exploded.
Figure 4B:
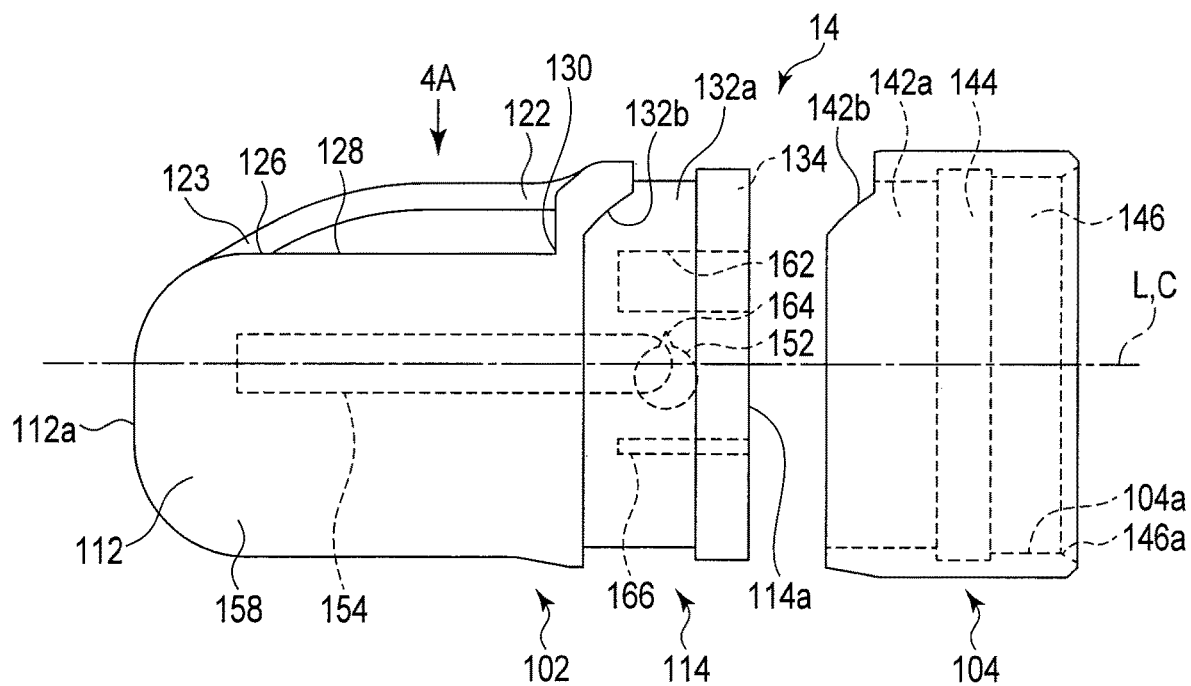
FIG. 4B is a view of a state seen from an arrow 4B side in FIG. 4A where the endoscope cover which is attached to the distal framing portion of the endoscope according to the first embodiment is exploded.

As shown in FIG. 4A to FIG. 4C, the endoscope cover 14 according to this embodiment includes a cover main body 102 which is attached to the distal framing portion 22 along the longitudinal axis of the insertion section 12, and a presser ring 104. The cover main body 102 is formed into an integral cylindrical shape by, for example, a resin material. The presser ring 104 is formed into a cylindrical shape or an annular shape by, for example, a rubber material. The cover main body 102 and the presser ring 104 are preferably made of an electrically insulating material. The inside diameters and inner peripheral surfaces 102a and 104a of the cover main body 102 and the presser ring 104 are formed into suitable sizes and shapes on the basis of the size of the distal framing portion 22.

The cover main body 102 has a closing portion 112 at its distal end, and an annular portion 114 at its proximal end. The closing portion 112 is formed into a substantially semispherical surface shape. The proximal end of the cover main body 102, that is, a proximal end 114a of the annular portion 114 is open.

Figure 5A:
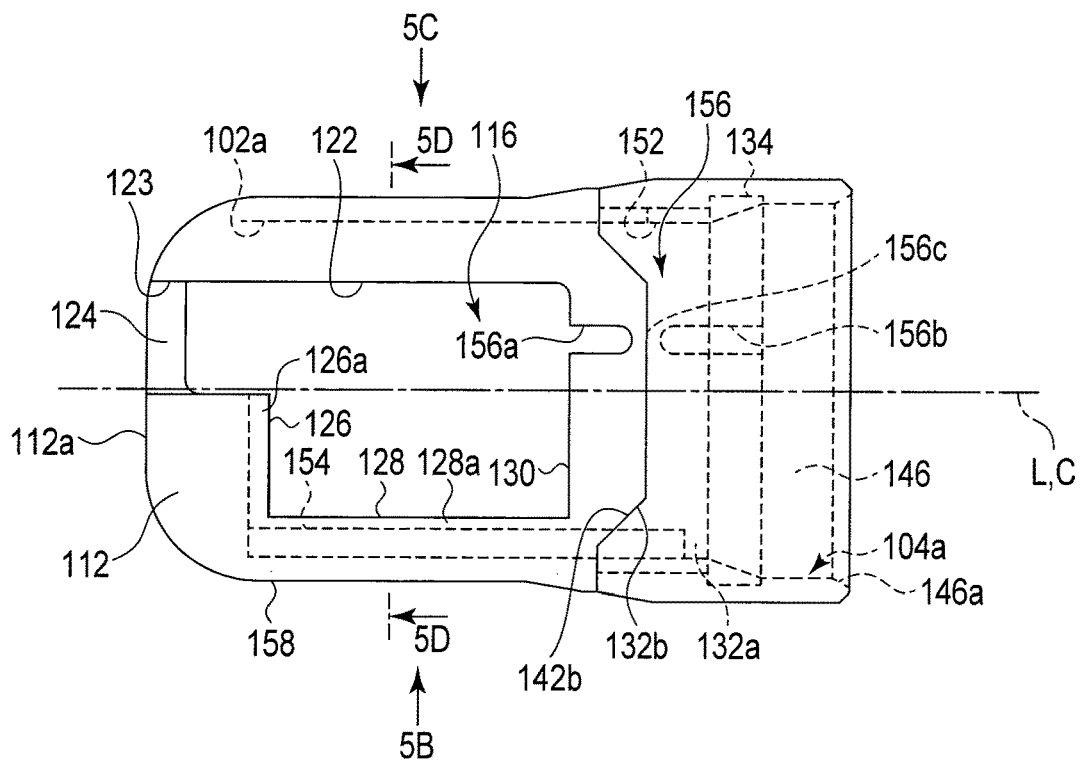
FIG. 5A is a schematic view showing the endoscope cover which is attached to the distal framing portion of the endoscope according to the first embodiment.
Figure 5B:
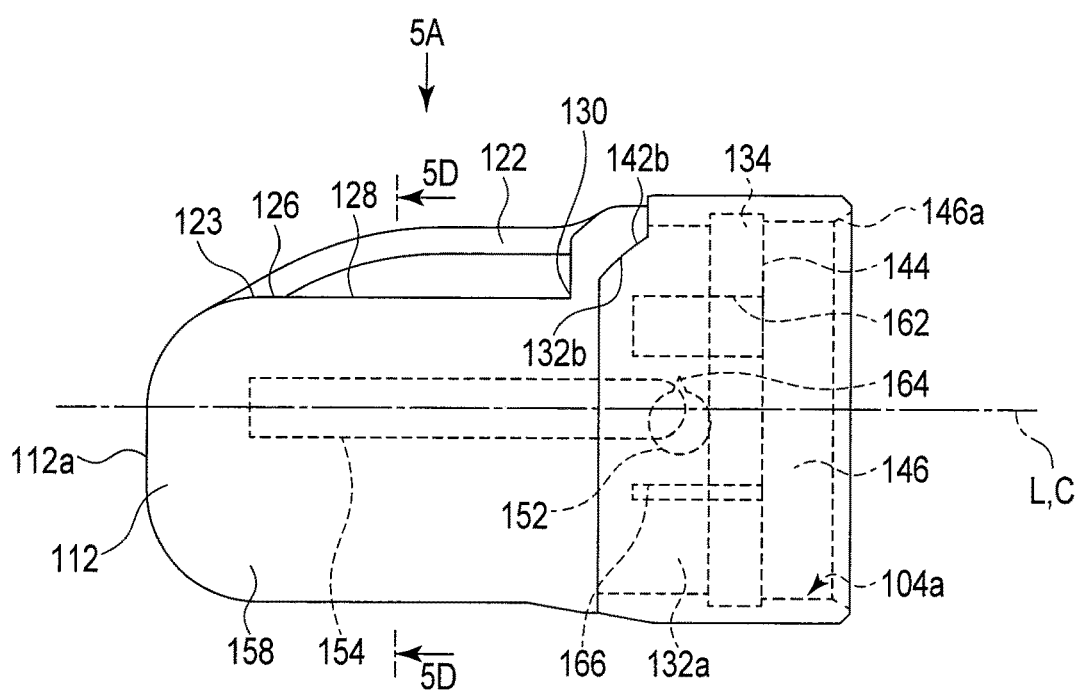
FIG. 5B is a view of the endoscope cover which is attached to the distal framing portion of the endoscope according to the first embodiment seen from an arrow 5B side in FIG. 5A.
Figure 5C:
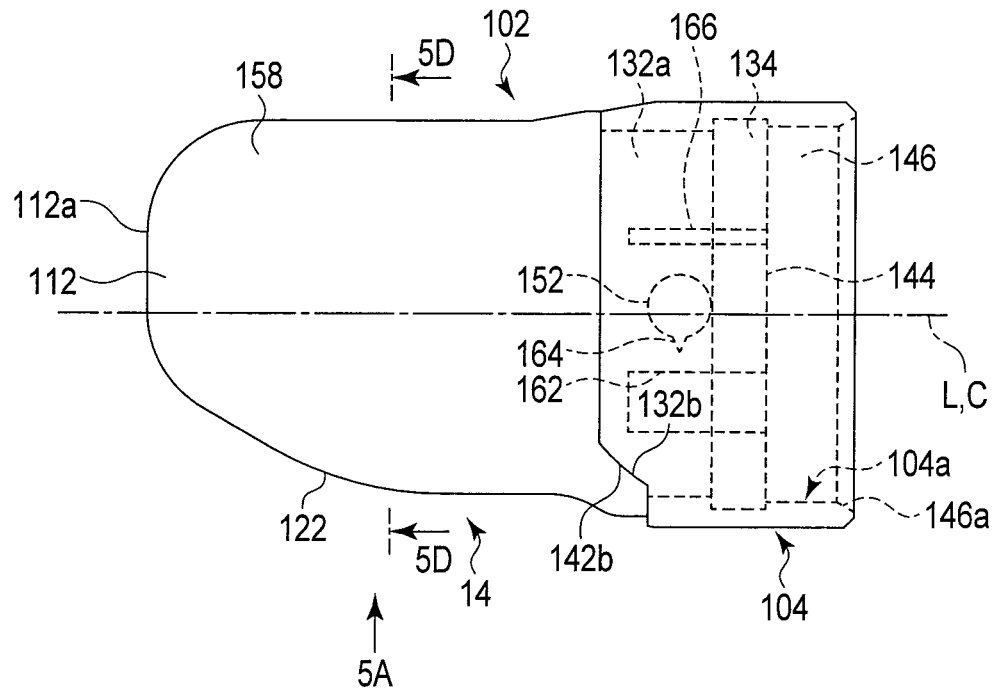
FIG. 5C is a view of the endoscope cover which is attached to the distal framing portion of the endoscope according to the first embodiment seen from an arrow 5C side in FIG. 5A.
Figure 5D:
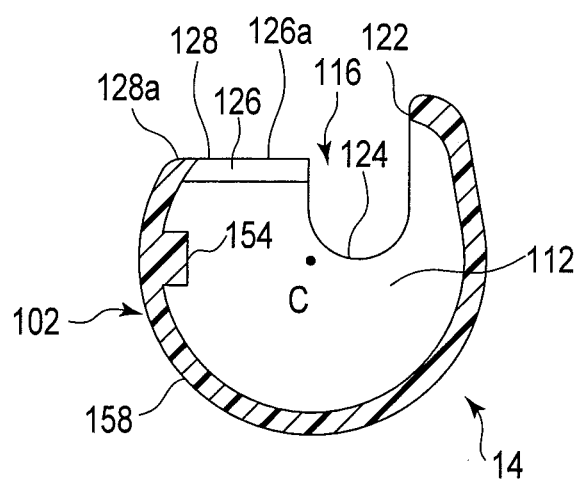
FIG. 5D is a schematic cross sectional view of the endoscope cover which is attached to the distal framing portion of the endoscope according to the first embodiment, taken along the line 5D-5D in FIG. 5A to FIG. 5C.

As shown in FIG. 5D, the cover main body 102 has an open edge 116 having a substantially C-shaped cross section between the closing portion 112 and the annular portion 114. The open edge 116 is open, for example, in the direction orthogonal to the longitudinal axis L. The open edge 116 exposes the illumination window 32a, the observation window 34a, the nozzle 35, and the swing table 42 of the distal framing portion 22 to the outside.

As shown in FIG. 5A, FIG. 5B, and FIG. 5D, the open edge 116 includes, from the proximal side toward the distal side along the longitudinal axis L, a right side edge 122 located on the right side, a U-shaped depressed portion 124 continuous with the right side edge 122, a distal side edge 126 continuous with the depressed portion 124, a left side edge 128 which is continuous with the depressed portion 124 and which is located on the left side from the proximal side to the distal side along the longitudinal axis, and a proximal side edge 130 located between the right side edge 122 and the proximal portion of the left side edge 128. The open edge 116 forms a closed ring by the right side edge 122, the depressed portion 124, the distal side edge 126, the left side edge 128, and the proximal side edge 130. The right side edge 122 and the left side edge 128 are preferably parallel or substantially parallel to each other. The distal side edge 126 and the proximal side edge 130 are preferably parallel or substantially parallel to each other.

The right side edge 122 cooperates with the annular portion 114 and a later-described turning peripheral surface 158 (see FIG. 5A to FIG. 5D) to movably cover the wire 44 of the swing mechanism 38. The distal side edge 126 has a distal side covering portion 126a which covers the distal side of the illumination window 32a of the flat portion 62 of the main body 52. Similarly, the left side edge 128 has a left side covering portion 128a which covers the left side of the illumination window 32a and the observation window 34a of the flat portion 62 of the main body 52.

The U-shaped depressed portion 124 is formed at the distal end of the right side edge 122 continuously with the right side edge 122. The depressed portion 124 is formed toward a distal end 112a of the closing portion 112. As shown in FIG. 5B and FIG. 5C, the part in which the depressed portion 124 is formed is tapered toward the distal side along the longitudinal axis L.

As shown in FIG. 4A, the annular portion 114 has, on its outer peripheral surface, a fit portion 132 to which the presser ring 104 is fitted. The fit portion 132 is circumferentially formed at a position away from the proximal side edge 130 of the open edge 116 toward the proximal side along the longitudinal axis L. The fit portion 132 includes an annular depressed portion 132a which inhibits the movement of the presser ring 104 with regard to the cover main body 102 along the longitudinal axis L, and a fit depressed portion 132b which inhibits the movement around the longitudinal axis L. The annular depressed portion 132a and the fit depressed portion 132b are integrally and continuously formed. The annular portion 114 has an annular flange portion 134 which is formed at the proximal end of the fit portion 132 and which diametrically outwardly protrudes with regard to the longitudinal axis L as compared to the annular depressed portion 132a. Formed on the inner periphery of the flange portion 134 is a skirt portion 134a which becomes thinner as it comes closer to the proximal side along the longitudinal axis L. The skirt portion 134a increases in inside diameter as it comes closer to the proximal side. The skirt portion 134a is preferably tapered.

In addition, it is appropriate that the inside diameter of the inner peripheral surface 102a of the cover main body 102 be constant from the vicinity of the distal end of the right side edge 122 of the open edge 116 and the vicinity of the distal end of the left side edge 128 to the distal end of the skirt portion 134a of the flange portion 134.

The presser ring 104 includes an annular protruding portion 142a which is formed in the inner peripheral surface 104a of the presser ring 104 and which is fitted to the annular depressed portion 132a, and a fit protruding portion 142b which is fitted to the fit depressed portion 132b. The presser ring 104 has an annular fit depressed portion 144 which is formed in the inner peripheral surface 104a of the presser ring 104 and to which the flange portion 134 is fitted on the proximal side of the annular protruding portion 142a. Thus, as shown in FIG. 5A to FIG. 5C, and FIG. 6, the presser ring 104 is fitted to the annular portion 114 of the cover main body 102. In addition, the presser ring 104 has a fit portion 146 which is formed in the inner peripheral surface 104a of the presser ring 104 and to which a thread wound portion 24a in the distal portion of the bending portion 24 is fitted on the proximal side of the fit depressed portion 144. A skirt portion 146a which becomes thinner as it comes closer to the proximal side along the longitudinal axis L is formed on the inner periphery of the proximal end of the fit portion 146. The skirt portion 146a increases in inside diameter as it comes closer to the proximal side. The skirt portion 146a is preferably tapered.

As shown in FIG. 4A, FIG. 5A, FIG. 5C, and FIG. 6, a lock depressed portion (depressed lock portion) 152 which can be locked to the lock pin 74 is formed in the inner peripheral surface 102a of the annular portion 114 at the proximal end of the cover main body 102. The lock depressed portion 152 may be formed in a state where the inner peripheral surface 102a and outer peripheral surface of the cover main body 102 communicate with each other, or may be simply formed to be depressed in the inner peripheral surface 102a of the cover main body 102. It is appropriate that the lock depressed portion 152 be formed in the annular depressed portion 132a.

A guide protruding portion (second guide) 154 movable along the guide groove 70 is formed in the inner peripheral surface 102a of the cover main body 102. That is, the guide protruding portion 154 diametrically inwardly protrudes from the inner peripheral surface 102a of the cover main body 102. Here, the guide protruding portion 154 is preferably formed from the vicinity of the distal end of the inner peripheral surface 102a of the cover main body 102 to the vicinity of its proximal end. While the guide protruding portion 159 can be formed into a suitable shape, its cross section is, for example, substantially rectangularly shaped as shown in FIG. 5D. Otherwise, although not shown, more than one guide protruding portion 151 may be spaced out at suitable intervals.

As shown in FIG. 4A and FIG. 4B, a fragile portion 156 is formed between the proximal side edge 130 of the open edge 116 of the cover main body 102 and the proximal end 114a of the flange portion 134 of the annular portion 114. The fragile portion 156 is lower in strength than other adjacent parts and is thus fragile, and is broken when the cover 14 is detached from the distal framing portion 22. Therefore, the fragile portion 156 is at least partly provided in the annular portion 114 of the cover main body 102, and is formed to break the annular portion 114 when stress is applied to the annular portion 114, and the fragile portion 156 is lower in strength than other parts of the annular portion 114. Here, the fragile portion 156 has slits 156a and 156b. One slit 156a is formed continuously with the proximal side edge 130 of the open edge 116. The other slit 156b is formed continuously with the proximal end 114a of the flange portion 134 of the annular portion 114. Here, the slits 156a and 156b are formed along the longitudinal axis L. The slits 156a and 156b are not in communication with each other, and a coupling portion 156c is formed therebetween. Thus, the annular depressed portion 132a of the annular portion 114 is annular. In addition, the lock depressed portion 152 is formed at a position substantially 90° away from the coupling portion 156c in a peripheral direction of the longitudinal axis L. The guide protruding portion 154 is formed at a position substantially 90° away from the coupling portion 156c in the peripheral direction of the longitudinal axis on the side opposite to the lock depressed portion 152. Thus, the fragile portion 156 is preferably located at a position substantially 90° away from each of the guide protruding portion 154 and the lock depressed portion 152 in the peripheral direction of the central axis C. That is, the guide protruding portion 154 is different in position from the lock depressed portion 152 in the peripheral direction of the longitudinal axis L. Although described later, it is preferable that the fragile portion 156 is more than 90° away from the guide protruding portion 154, and the positions of the guide protruding portion 154 and the fragile portion 156 are preferably closer to each other than the positions of the fragile portion 156 and the lock depressed portion 152.

In this embodiment, the fragile portion 156 is preferably formed not in the flat portion 62 of the main body 52 of the distal framing portion 22 but on the wire moving portion (wire moving space) 68. The slit 156b on the proximal side contributes to the elastic deformation of the annular portion 114. That is, the flange portion 134 is elastically deformed when the lock depressed portion 152 is locked to the lock pin 74.

As shown in FIG. 4A to FIG. 4C, the annular port on 114 at the proximal end of the cover main body 102 has a groove (lock pin guide groove) 162 in a part including the proximal end 114a of the annular portion 114 of the cover main body 102 along the longitudinal axis L. The groove 162 is provided at a position adjacent to the lock depressed portion 152 in the peripheral position around the longitudinal axis L. The groove 162 is permitted to have a suitable shape. Here, as shown in FIG. 4C, the groove 162 has a corner portion 162a at its distal end. The groove 162 is formed by parallel edges from its distal end toward its proximal end.

The lock pin 74 is disposed in the groove 162 when the cover main body 102 is turned with respect to the distal framing portion 22 in the peripheral direction of the longitudinal axis L and then the lock pin 74 is unlocked from the lock depressed portion 152. It is appropriate that the width (inter-edge distance) of the groove 162 along the peripheral direction of the longitudinal axis L be formed to be equal to or more than the width of the lock pin 74 of the distal framing portion 22 along the peripheral direction of the longitudinal axis L.

A second fragile portion 164 which is broken when the lock pin 74 is moved from the lock depressed portion 152 to the groove 162 is provided between the lock depressed portion 152 and the groove 162. In this embodiment, the second fragile portion 164 is formed as a slit which is formed from the lock depressed portion 152 toward the groove 162. The second fragile portion 164 is preferably formed integrally with the lock depressed portion 152. In addition, the second fragile portion 164 does not necessarily need to be continuous with the groove 162.

As shown in FIG. 4B and FIG. 4C, the annular portion 114 at the proximal end of the cover main body 102 has an additional groove (deformation permitting portion) 166 in a part including the proximal end 114a of the annular portion 114 of the cover main body 102 along the longitudinal axis L. The additional groove 166 is provided at a position adjacent to the lock depressed portion 152 in the peripheral direction of the longitudinal axis L. The groove 162 is permitted to have a suitable shape. The lock depressed portion 152 is between the groove 162 and the additional groove 166. The additional groove 166 is used to elastically deform the lock depressed portion when the lock pin 74 is locked to the lock depressed portion 152. Although described later, the additional groove 166 is also used to elastically deform a region including the lock depressed portion 152 when the second fragile portion 164 between the lock depressed portion 152 and the groove 162 is broken (see FIG. 14B).

As shown in FIG. 5A to FIG. 5D, the cover main body 102 has, in its outer periphery, the turning peripheral surface 158. The turning peripheral surface 158 is formed as a part of a circular cylinder. The central axis C of the cover 14 and the distal framing portion 22 is defined by the turning peripheral surface 158. This turning peripheral surface 158 is fitted to a later-described support peripheral surface 214 of a jig 200.

When the cover 14 is formed, the presser ring 104 is attached to the cover main body 102 shown in FIG. 4A. At this point, it is first ascertained that the coupling portion 156c is present between the slits 156a and 156b of the cover main body 102, and the slits 156a and 156b are not continuous with each other. Then, as shown in FIG. 5A to FIG. 5C, the presser ring 104 is fitted to the cover main body 102 to form the cover 14.

Figure 6:
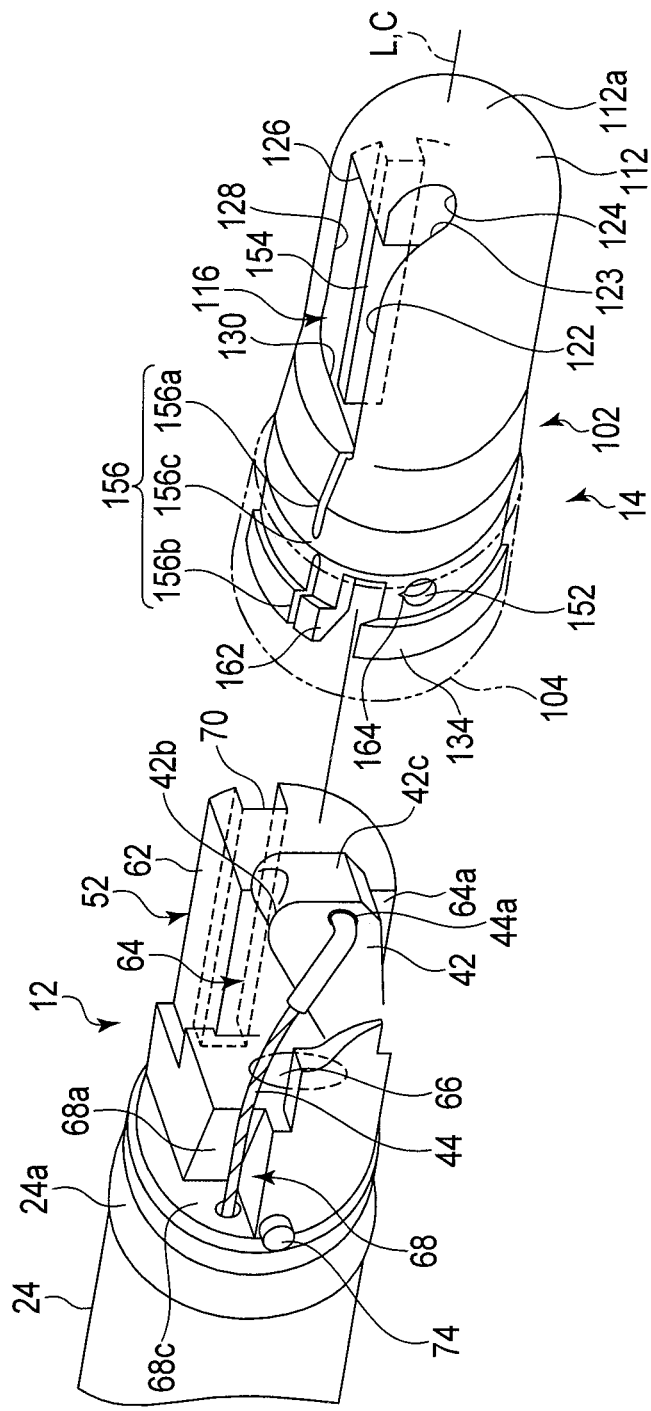
FIG. 6 is a schematic perspective view snowing a state where the endoscope cover is to be attached to the distal framing portion of the endoscope according to the first embodiment.

As shown in FIG. 6, the direction of the cover 14 in the peripheral direction of the longitudinal axis L is defined, and the cover 14 is then attached to the distal framing portion 22. At this point, the guide protruding portion 154 of the cover 14 is fitted to the guide groove 70 of the main body 52 of the distal framing portion 22 and then moved along the longitudinal axis L. This prevents the displacement of the cover 14 with respect to the distal framing portion 22 in the peripheral direction.

Furthermore, when the cover 14 is attached to the distal framing portion 22, the skirt portion 146a of the fit portion 146 of the presser ring 104 of the cover 14 abuts on the lock pin 74 of the distal framing portion 22. At this point, the fit portion 146 is elastically deformed due to its elasticity. Thus, the lock pin 74 of the distal framing portion 22 abuts on the skirt portion 134a of the annular portion 114 of the cover main body 102. At this point, the annular portion 114 is elastically deformed by the slit 156*b*, the groove 162, and the additional groove 166. Thus, the lock depressed portion 152 engages with the lock pin 74 of the distal framing portion 22. Further, the displacement of the cover 14 with respect to the distal framing portion 22 in the axial direction and the peripheral direction is prevented.

Figure 7:
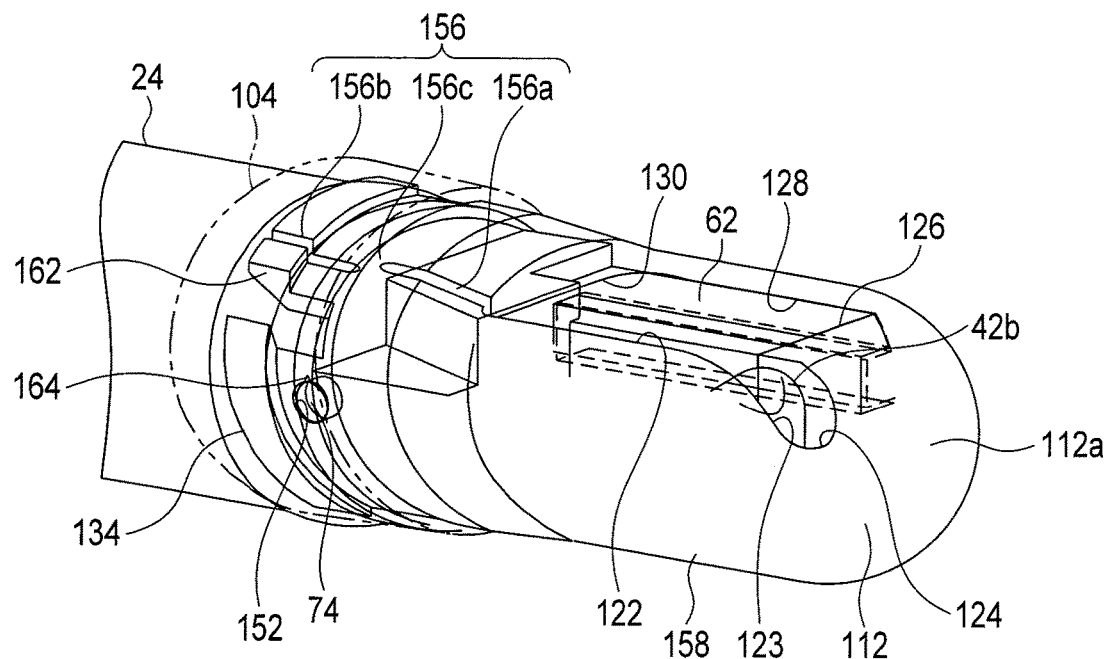
FIG. 7 is a schematic perspective view showing a state where the endoscope cover is attached to the distal framing portion of the endoscope according to the first embodiment.
Figure 8A:
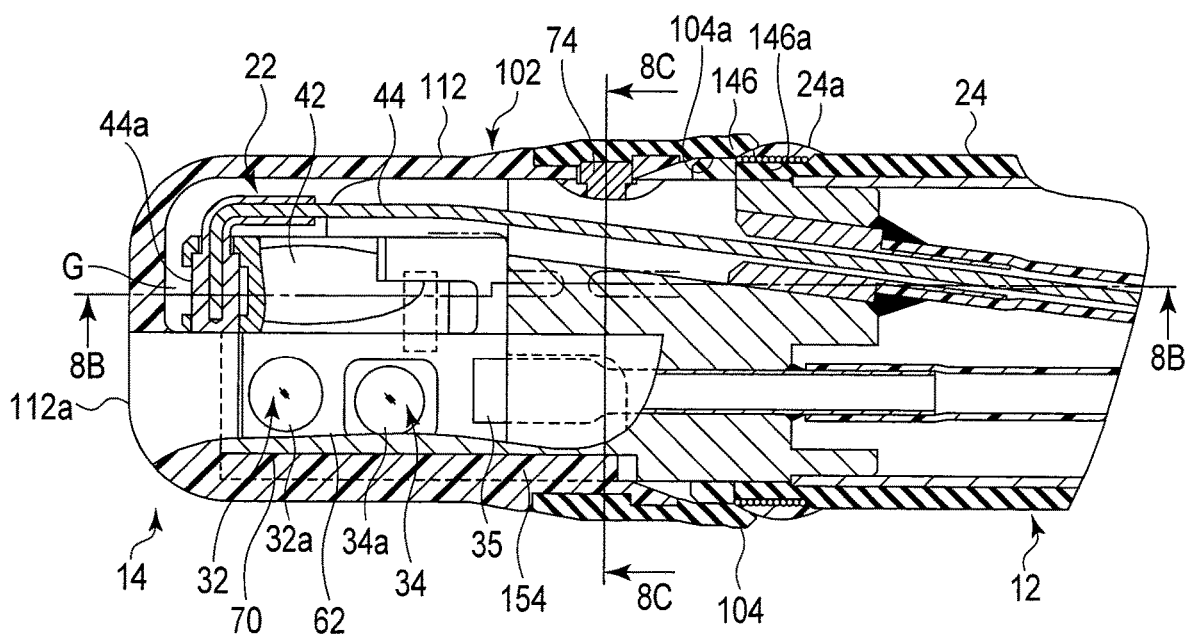
FIG. 8A is a schematic partial longitudinal sectional view showing a state where the endoscope cover is attached to the distal framing portion of the endoscope according to the first embodiment.
Figure 8B:
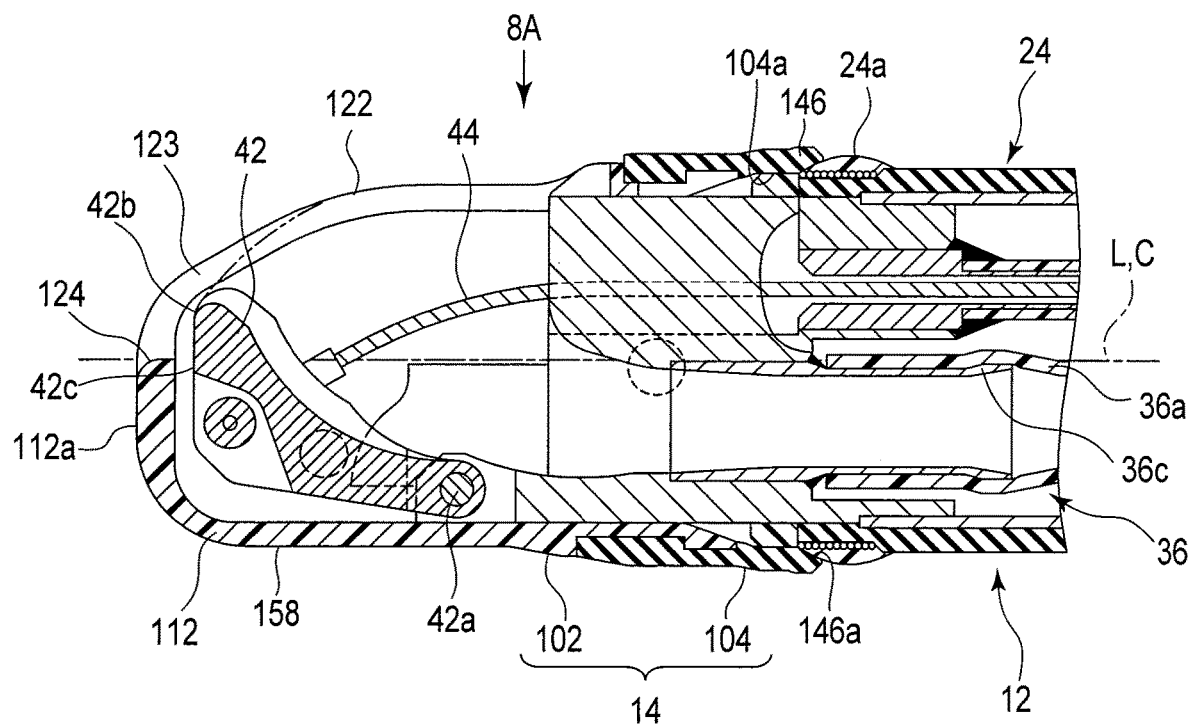
FIG. 8B is a schematic sectional view of the endoscope cover which is attached to the distal framing portion of the endoscope according to the first embodiment, taken along the line 8B-8B FIG. 8A.
Figure 8C:
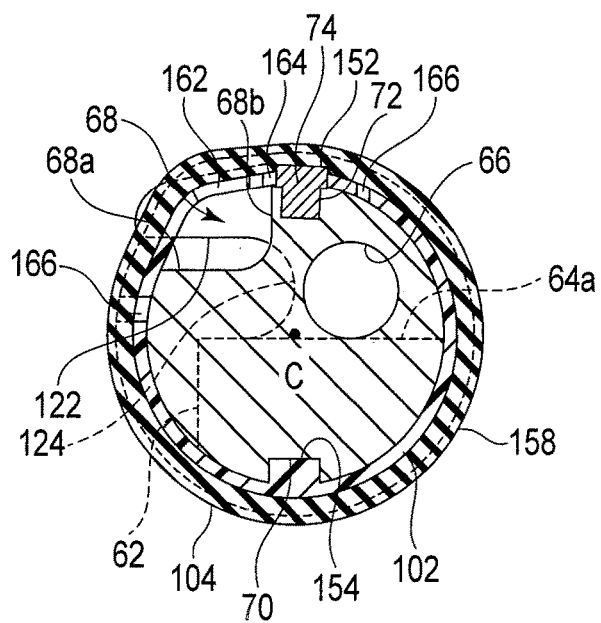
FIG. 8C is a schematic sectional view of the endoscope cover which is attached to the distal framing portion of the endoscope according to the first embodiment, taken along the line 8C-8C in FIG. 8A.

As shown in FIG. 7 to FIG. 8B, for example, the skirt portion 146*a* of the fit portion 146 of the presser ring 104 abuts on the thread wound portion 24*a* at the distal end of the bending portion 24. Moreover, the thread wound portion 24*a* is a part in which an adhesive agent is applied from the outer periphery of an annularly wound thread and this coating adhesive agent is then fixed.

Figure 9:
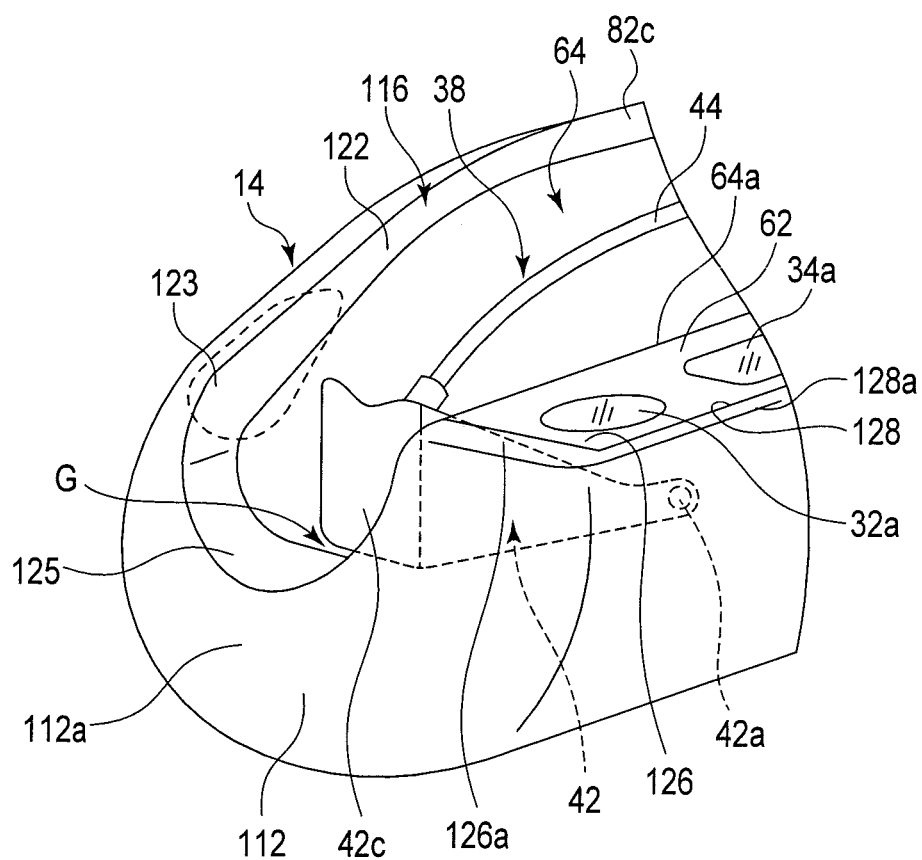
FIG. 9 is a schematic perspective view showing the vicinity of a distal portion in a state where the endoscope cover is attached to the distal framing portion of the endoscope according to the first embodiment.

At this point, as shown in FIG. 7 to FIG. 9, the illumination window 32*a*, the observation window 34*a*, and the nozzle 35 are exposed from the open edge 116 of the cover 14, and the swing table 42 is exposed swingably in a suitable range. In a state where the cover 14 is properly attached to the distal framing portion 22, a part of the distal face 42*c* and the distal end portion 42*b* of the swing table 42 are exposed when seen from the distal side along the longitudinal axis L. Thus, when the unshown treatment instrument is guided by the swing table 42 and then protrudes from the distal end of the swing table 42, the interference of the treatment instrument with the cover 14 can be prevented by the depressed portion 124. In addition, to prevent friction between the swing table 42 and the cover main body 102 in a state where the cover main body 102 is properly attached to the distal framing portion 22, a gap G is formed between the swing table 42 and the cover main body 102. That is, the gap G is formed between the distal face 42*c* of the swing table 42 and the depressed portion 124 of the cover 14. Even if the swing table 42 is swung, the gap amount varies but the presence of the gap is maintained between the distal face 42*c* of the swing table 42 and the depressed portion 124 of the cover 14. This prevents the motion of the swing table 42 from being blocked by the cover main body 102. In the outer peripheral surface through a cross section in a state where the cover 14 is attached to the distal framing portion 22, a part indicated with a reference number 158 forms a part of a circular ring.

The cover 14 is seen in a section perpendicular to the longitudinal axis L and then the section is divided into the first region and the second region different from each other as described above in a state where the cover 14 is attached to the distal framing portion 22, in which case the lock depressed portion 152 is located in the first region and the guide protruding portion 154 is located in the second region.

In a state where the cover 14 is attached to the distal framing portion 22, the insertion section 12 of the endoscope 10 is inserted into a duct such as a lumen, and observation and a suitable treatment are conducted. Moreover, the fragile portion 156 and the second fragile portion 164 are covered and protected by the presser ring 104. Thus, the breakage of the fragile portion 156 is inhibited even if the fragile portion 156 abuts on a lining or the like, for example, during the insertion into a duct in a body cavity or the like or during a treatment.

After the use of the endoscope 10, the cover 14 is detached from the distal framing portion 22. The cover main body 102 and the presser ring 104 of the cover 14 are disposed of as they are. The distal framing portion 22 is washed, disinfected, and sterilized in a state the cover 14 is detached therefrom, and the distal framing portion 22 is reused. That is, the endoscope 10 is washed, disinfected, and sterilized in a state the cover 14 is detached therefrom, and the endoscope 10 is reused. At this point, because the cover 14 is detached from the distal framing portion 22, it is easy to wash not only the vicinity of the illumination window 32*a* of the illumination optical system 32 and the vicinity of the observation window 34*a* of the observation optical system 34 but also the channel 36 and the swing mechanism 38.

Moreover, when the cover 14 is detached from the distal framing portion 22, the coupling portion 156*c* and the second fragile portion 164 between the slits 156*a* and 156*b* are torn by use of force of the user's fingers, and the lock depressed portion 152 is unlocked from the lock pin 74 of the distal framing portion 22. In this case, the cover 14 is turned with respect to the distal framing portion 22 around the central axis C so that the lock pin 74 of the distal framing portion 22 is disposed in the groove 162 from the lock depressed portion 152 through the second fragile portion 164. After the lock depressed portion 152 is unlocked from the lock pin 74 as above, it is not impossible to move the cover 14 to the distal side with respect to the central axis C and then detach the cover 14. However, when the cover 14 is detached from the distal framing portion 22 by the user's fingers, the way of detachment can differ from user to user. There is therefore concern that it may become difficult to stably break the fragile portion 156 and the second fragile portion 164.

The fragile portion 156 and the second fragile portion 164 can be stably broken by use of the jig (a detachment tool for the cover 14) 200 (see FIG. 10 to FIG. 13B) described below. It is therefore appropriate to use the jig 200 when the cover 14 is detached from the distal framing portion 22 after the use of the endoscope 10. The jig 200 is also used to certainly break the cover 14 to prevent the reuse of the cover 14.

Figure 10:
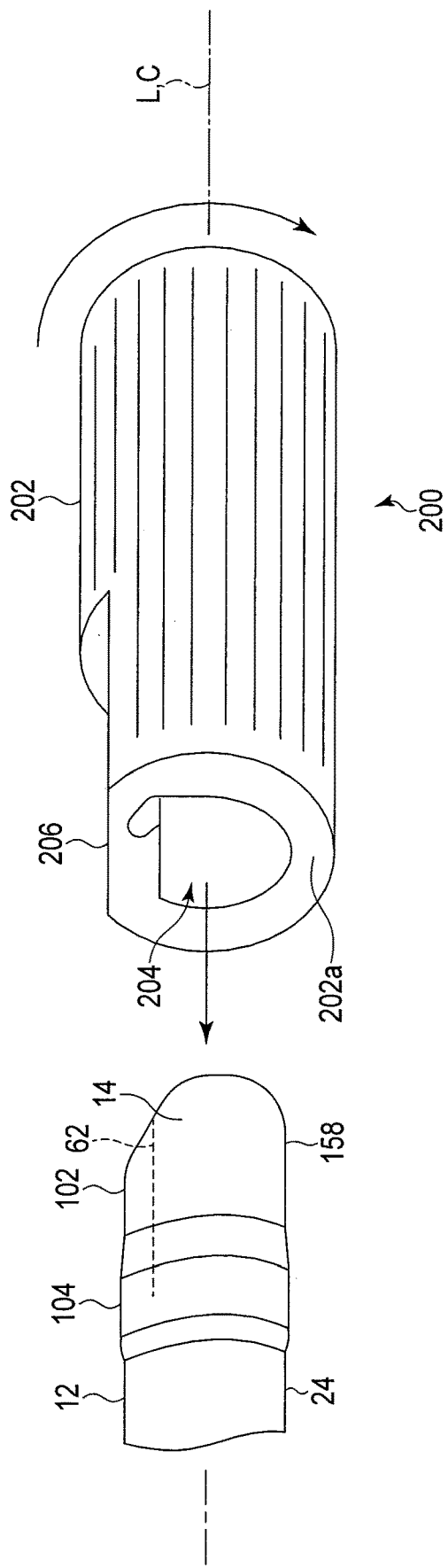
FIG. 10 is a schematic perspective view showing a state where the endoscope cover attached to the distal framing portion of the endoscope according to the first and second embodiments is to be detached by use of a jig.
Figure 11A:
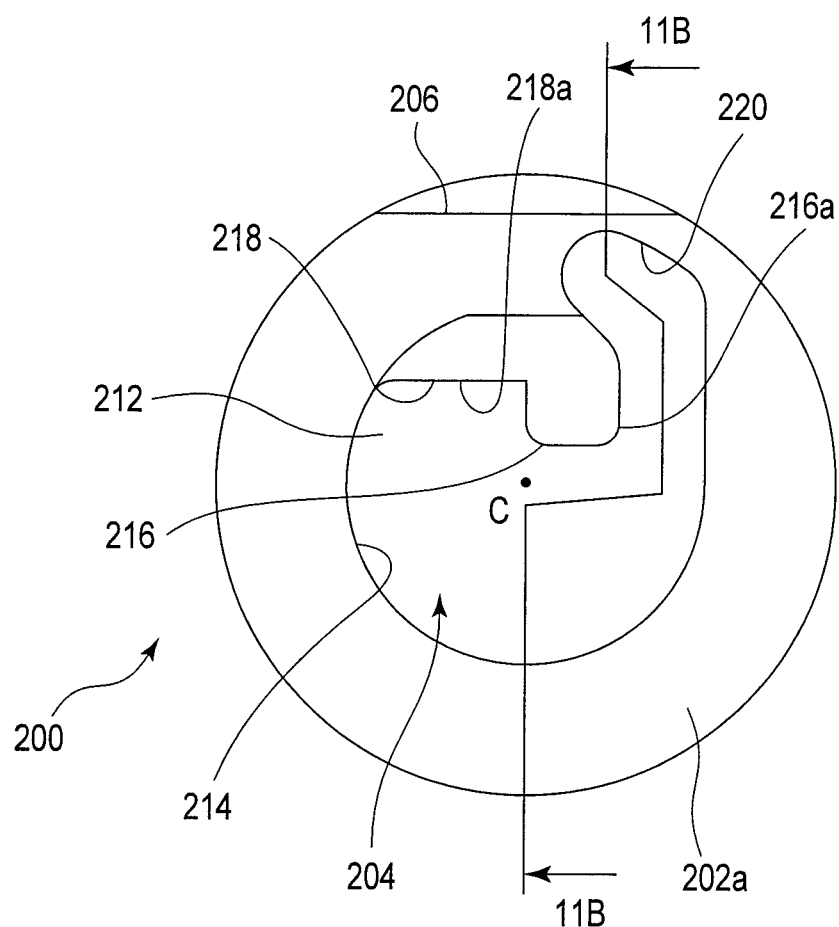
FIG. 11A is a schematic front view showing an active portion at one end of the jig which detaches the endoscope cover attached to the distal framing portion of the endoscope according to the first and second embodiments.
Figure 11B:
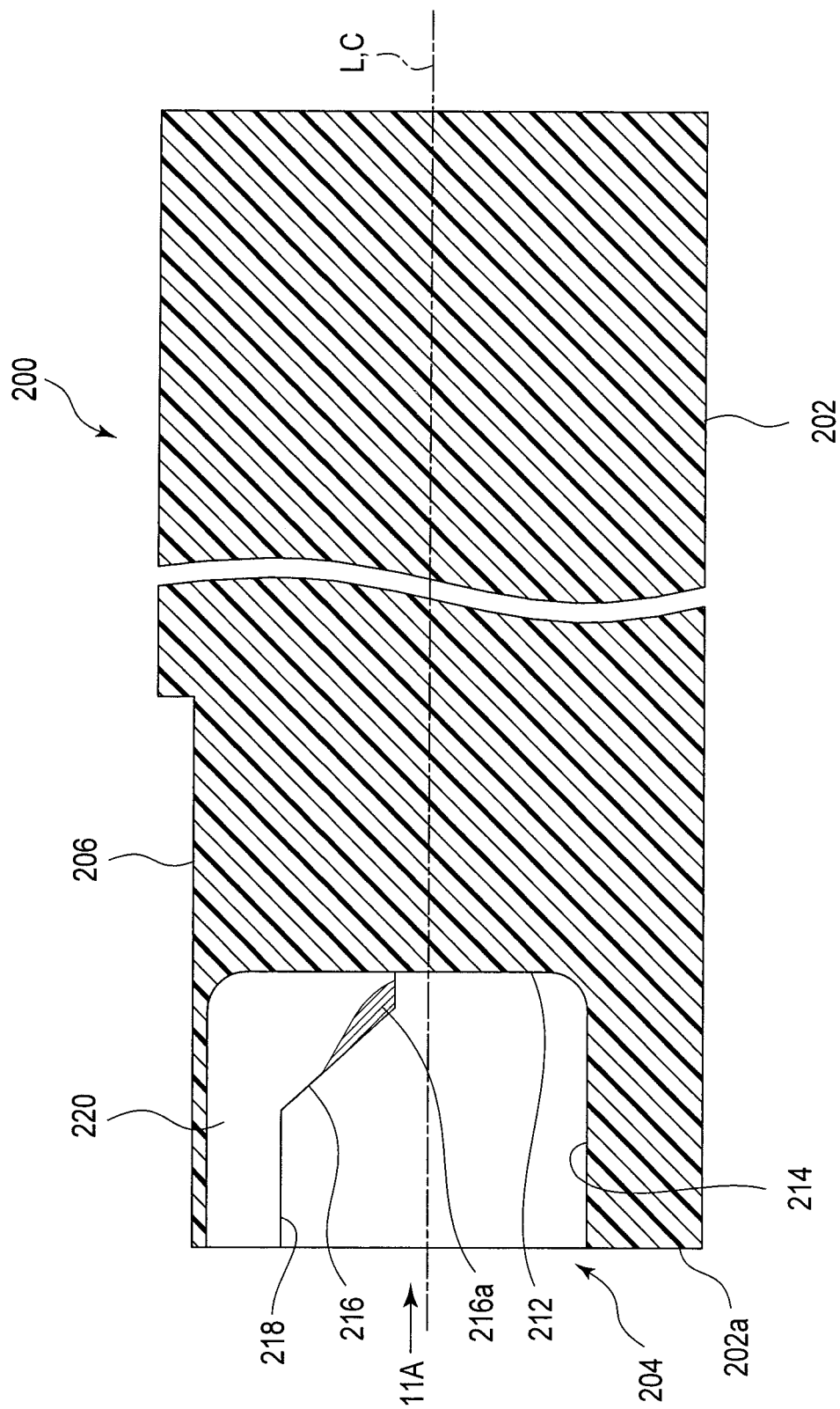
FIG. 11B is a schematic longitudinal sectional view of the active portion at one end of the jig which detaches the endoscope cover attached to the distal framing portion of the endoscope according to the first and second embodiments, taken along the line 11B-11B in FIG. 11A.

The cover detachment jig 200 according to the present embodiment is made of a rigid material such as a resin material or a metallic material that is more rigid than the cover main body 102 of the cover 14. As shown in FIG. 10, the jig 200 has a column 202. The outer periphery of the column 202 is formed into a suitable shape. As shown in FIG. 11A and FIG. 11B, an active portion 204 which acts when the cover 14 attached to the distal framing portion 22 is detached is formed at one end 202*a* of the column 202. The active portion 204 is formed into a depressed shape which covers the vicinity of the distal end 112*a* of the closing portion 112 of the cover 14. An index 206 which allows the user to recognize the direction of the jig 200 in the peripheral direction of the longitudinal axis L is formed in the jig 200 on the outer peripheral surface of the column 202. Here, the index 206 is formed as a plane such that the direction can be recognized by touching. It is appropriate that the index 206 be formed at a position adjacent to the active portion 204.

The index 206 permits the user to, for example, visually recognize the position to insert into the distal framing portion 22 to which the endoscope cover 14 is attached. The index may be a character such as "up", or may be an imprinted arrow indicating a rotation direction. Thus, the outer shape of the cover detachment jig 200 is not specifically limited.

As shown in FIG. 11A and FIG. 11B, the active portion 204 has a bottom surface 212, the support peripheral surface 214 which is preferably orthogonal to the bottom surface 212, a first protruding portion 216 which is fitted to the U-shaped depressed portion 124 of the open edge 116 of the cover 14, a second protruding portion 218 which is fitted to the distal side covering portion 126*a* of the cover 14, and a relief portion 220 in which a part of the right side edge 122 of the open edge 116 of the broken cover 14 is disposed.

Figure 12A:
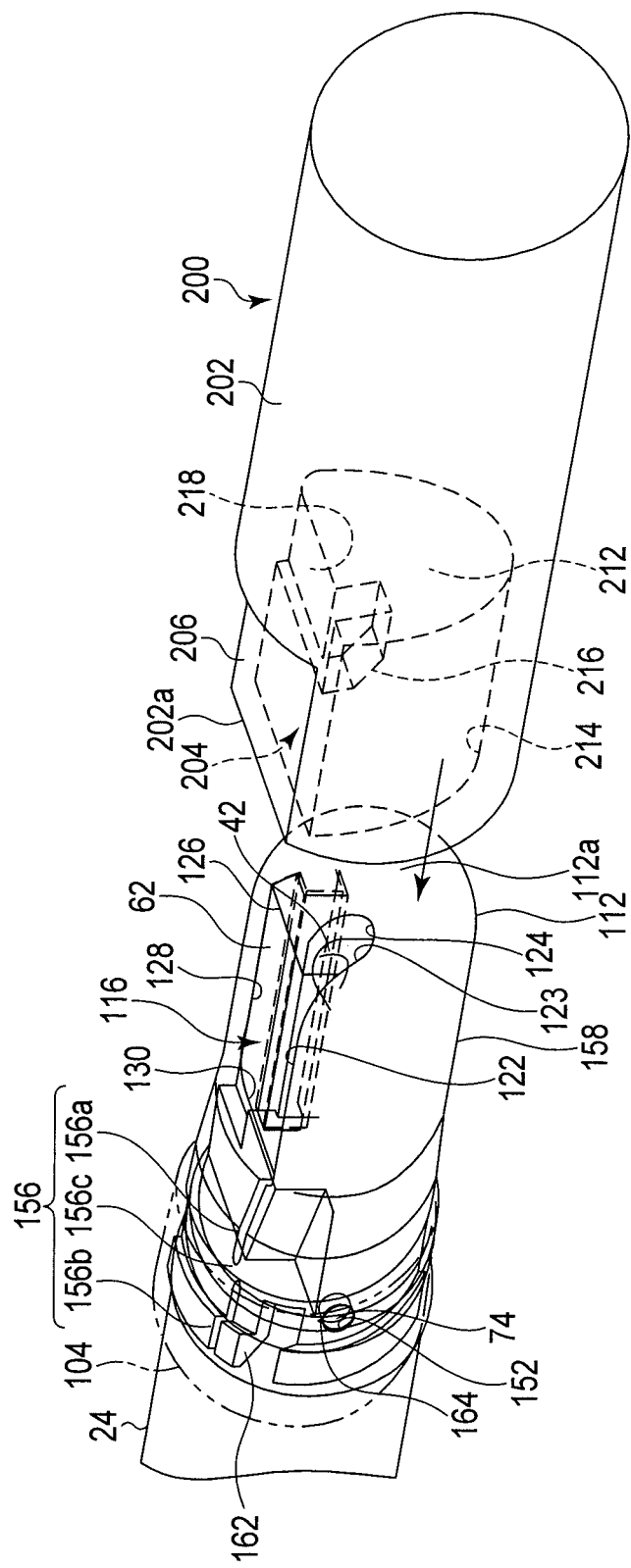
FIG. 12A is a schematic perspective view showing a state where the jig is to be fitted to the cover to detach the endoscope cover attached to the distal framing portion of the endoscope according to the first embodiment.
Figure 13A:
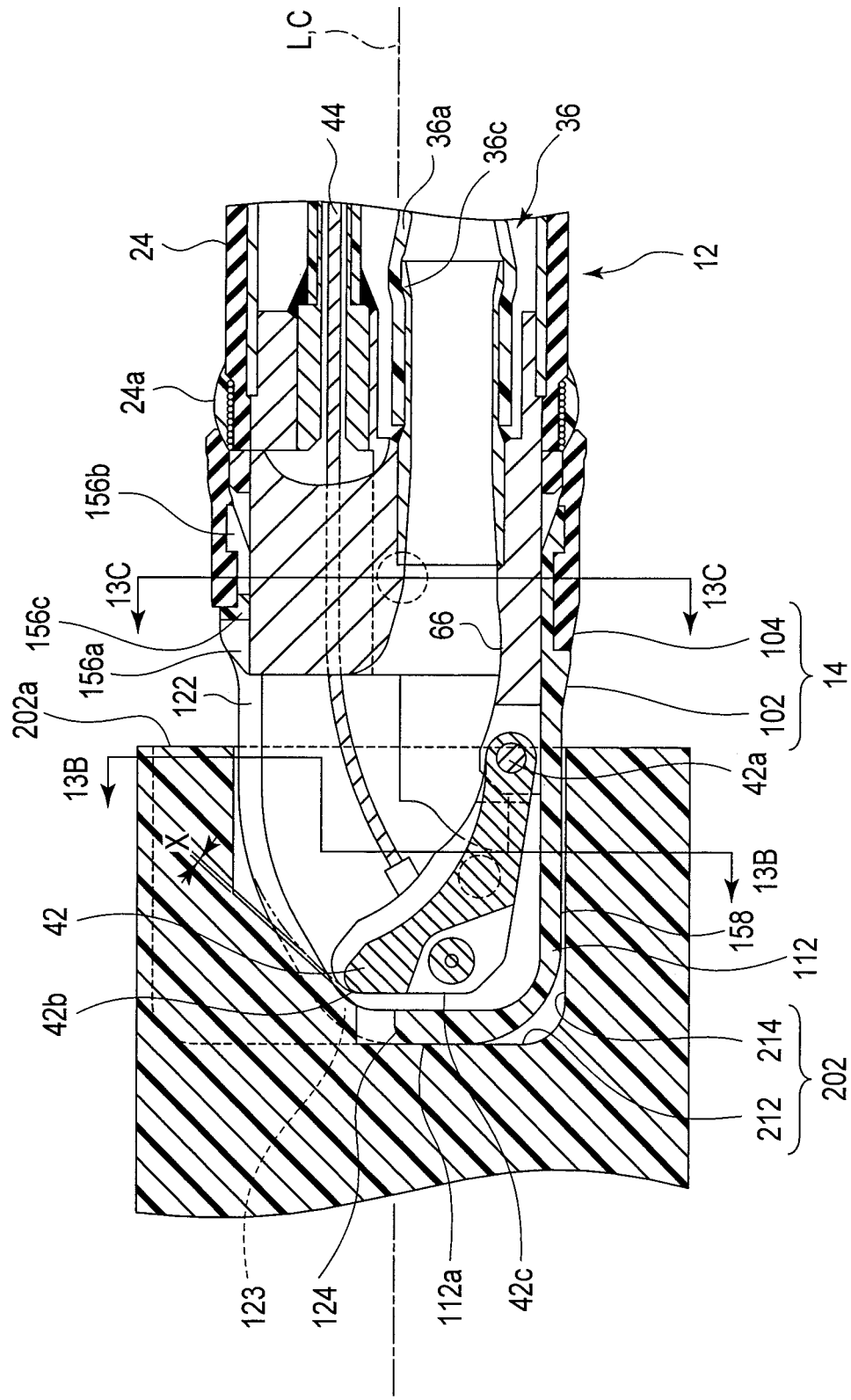
FIG. 13A is a schematic longitudinal sectional view showing a state where the jig is fitted to the cover to detach the endoscope cover attached to the distal framing portion of the endoscope according to the first embodiment.

As shown in FIG. 13A and FIG. 12B, the active portion 204 at the one end 202a of the column 202 of the jig 200 is fitted to the distal framing portion 22 to which the endoscope cover 14 is attached.

As shown in FIG. 13A, the distal end 112a of the closing portion 112 of the cover 14 abuts on the bottom surface 212. Thus, the length of the cover 14 to be put in the depressed active portion 204 of the one end 202a of the jig 200 is regulated at a certain length by the bottom surface 212.

Figure 13B:
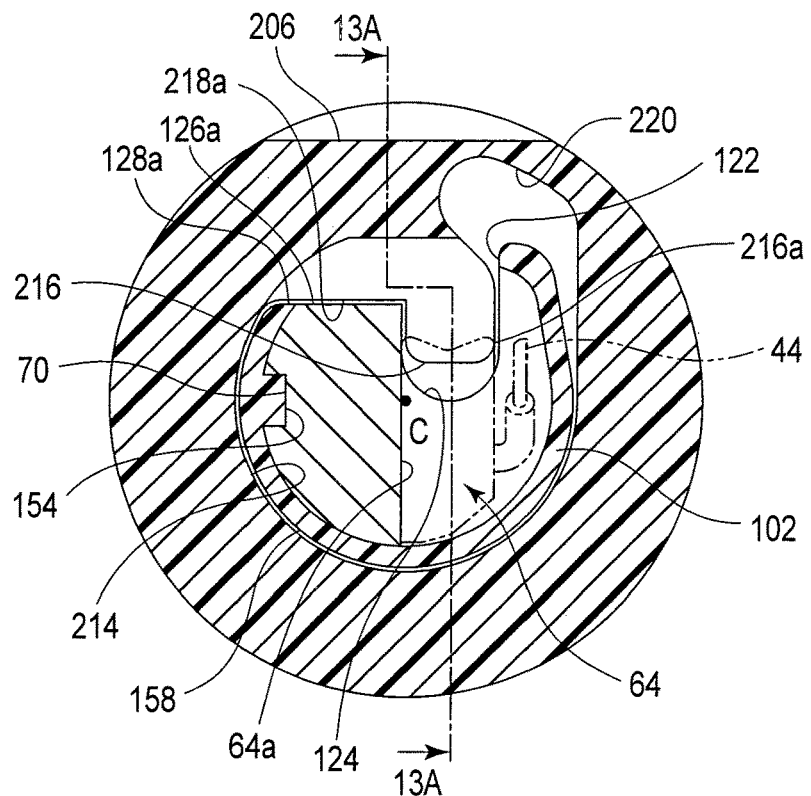
FIG. 13B is a schematic cross sectional view taken along the line 13B-13B in FIG. 13A.

As shown in FIG. 13A and FIG. 13B, the support peripheral surface 214 is formed as a part of the circular cylinder. The central axis C of the active portion 204 is defined by the support peripheral surface 214. The distance between the central axis C and the support peripheral surface 214, that is, the radius is formed to be slightly larger than the radius defined by the turning peripheral surface 158 which forms a part of the circular cylinder of the cover 14. Thus, the turning peripheral surface 158 of the cover 14 abuts on and is thus supported on the support peripheral surface 214. At this point, the support peripheral surface 214 is movable relative to the turning peripheral surface 158 around the central axis C.

As shown in FIG. 11A and FIG. 13A, the first protruding portion 216 protrudes toward the one end 202a of the jig 200 with respect to the bottom surface 212. The amount of protrusion of the first protruding portion 216 with respect to the bottom surface 212 is adjusted so that the first protruding portion 216 can abut on the depressed portion 124 of the cover 14 but is located away from the distal end portion 42b and the distal face 42c of the swing table 42 in a state where the distal end 112a of the closing portion 112 of the cover 14 is in abutment with the bottom surface 212. Even if the swing table 42 is suitably swung in a state where the distal end 112a of the closing portion 112 of the cover 14 is in abutment with the bottom surface 212, the first protruding portion 216 does not abut on the distal end portion 42b and the distal face 42c of the swing table 42. Moreover, the width of the first protruding portion 216 is formed to be slightly smaller than the width of the depressed portion 124 of the cover 14. Thus, the first protruding portion 216 of the jig 200 has a pressure portion 216a which abuts on a pressure receiving portion 123 (see FIG. 9) between the depressed portion 124 of the open edge 116 of the cover 14 and the right side edge 122 if the jig 200 is turned with respect to the cover 14 in the peripheral direction of the central axis C.

The second protruding portion 218 shown in FIG. 11A protrudes toward the one end 202a of the column 202 with respect to the bottom surface 212. The second protruding portion 218 is adjacent to the first protruding portion 216 in the peripheral direction of the central axis C. The second protruding portion 218 has a counter surface 218a which is preferably parallel to the distal side covering portion 126a. The counter surface 218a can abut on the distal side covering portion 126a of the distal side edge 126 of the cover 14. Thus, the counter surface 218a can indirectly hold the flat portion 62 of the main body 52 of the distal framing portion 22.

How to use the jig 200 to detach the cover 14 attached to the distal framing portion 22 is described.

As shown in FIG. 10 and FIG. 12A, the active portion 204 of the jig 200 is put face to face with the distal framing portion 22 to which the cover 14 is attached. The direction of the index 206 is made parallel to the flat portion 62 of the distal framing portion 22. As shown in FIG. 12B, in this state, the active portion 204 of the jig 200 is fitted to the cover 14. The central axis C of the support peripheral surface 214 of the jig 200 is aligned with the central axis C of the turning peripheral surface 158 of the cover 14, and the distal end 112a of the closing portion 112 of the cover 14 is brought into abutment with the bottom surface 212 of the active portion 204 of the jig 200.

As shown in FIG. 13A, at this point, the first protruding portion 216 of the jig 200 is fitted to the depressed portion 124 of the open edge 116 of the cover 14. The second protruding portion 218 of the jig 200 is close to or in abutment with the distal side covering portion 126a of the cover 14. The second protruding portion 218 supports the position close to the distal side edge 126 between the distal side edge 126 and the distal end 112a of the closing portion 112.

In addition, even if the swing table 42 is swung and thereby disposed at any position, a gap (a distance between the first protruding portion 216 and the distal end portion 42b of the swing table 42 in FIG. 11A to FIG. 12A) X is formed between the first protruding portion 216 and the swing table 42. Thus, at any position in a swingable range, the swing table 42 does not contact the jig 200.

In a state where the distal framing portion 22 or the vicinity of the distal portion of the insertion section 12 is held and the distal end 112a of the closing portion 112 of the cover 14 is in abutment with the bottom surface 212 of the jig 200, the jig 200 is rotated with respect to the distal framing portion 22 and the cover 14 in a direction indicated by an arrow R in FIG. 12B. That is, the support peripheral surface 214 of the jig 200 having the common central axis C is turned around the central axis C with respect to the turning peripheral surface 158 of the cover 14.

Figure 13C:
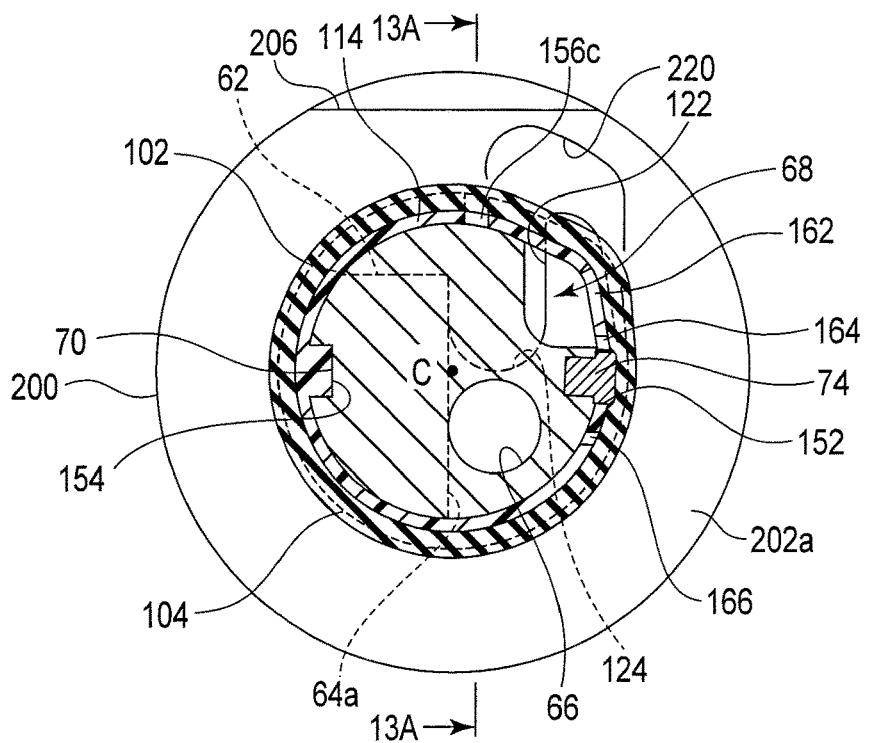
FIG. 13C is a schematic cross sectional view taken along the line 13C-13C in FIG. 13A.
Figure 13D:
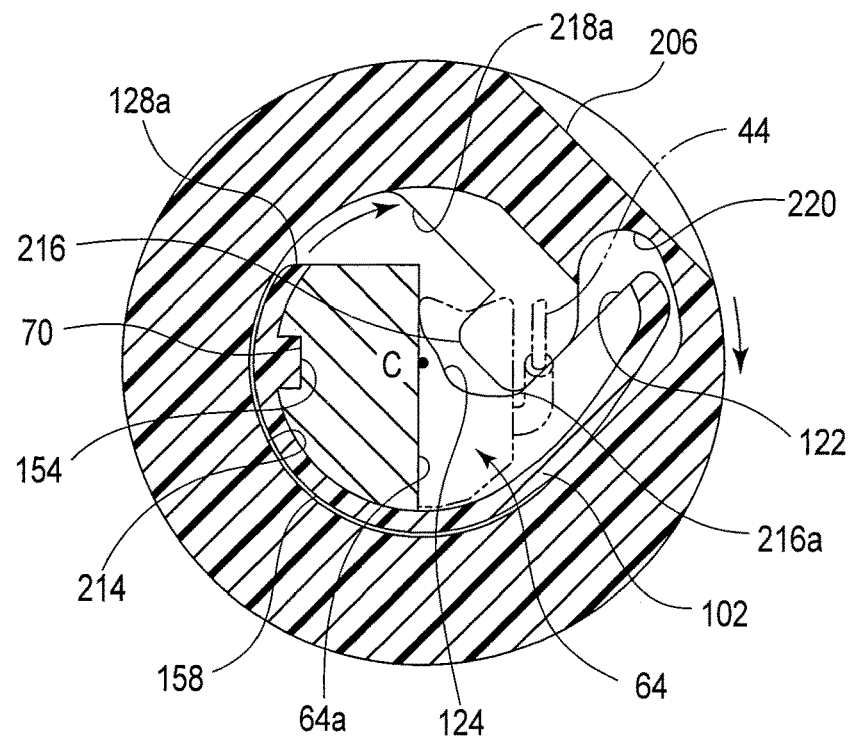
FIG. 13D is a schematic cross sectional view showing a state where the jig is twisted with respect to the cover from the state shown in FIG. 13B in a state where the jig is fitted to the cover, and a right edge of an opening edge is then pressed to open a depressed portion.

As shown in FIG. 13B and FIG. 13D, while the counter surface 218a of the second protruding portion 218 of the jig 200 is moved away from the distal side covering portion 126a of the cover 14, the pressure receiving portion 123 between the right side edge 122 of the open edge 116 and the depressed portion 124 is pressed by the pressure portion 216a of the first protruding portion 216.

Here, breaking stress of the guide protruding port on (second regulation portion) 154 of the cover 14 resulting from force applied around the central axis C of the distal framing portion 22 is set to be greater than the total of the amount of force which breaks the fragile portion 156 and the amount of force which unlocks the lock depressed portion 152 from the lock pin 74 when stress is applied to the cover main body 102 around the central axis C in a state where the cover main body 102 is attached to the distal framing portion 22. That is, the guide protruding portion 154 of the cover 14 keeps fitted to the guide groove 70 of the distal framing portion 22. Thus, the guide protruding portion (second restriction portion) 154 restricts the movement of the cover main body 102 with respect to the distal framing portion 22 around the central axis C.

Figure 13E:
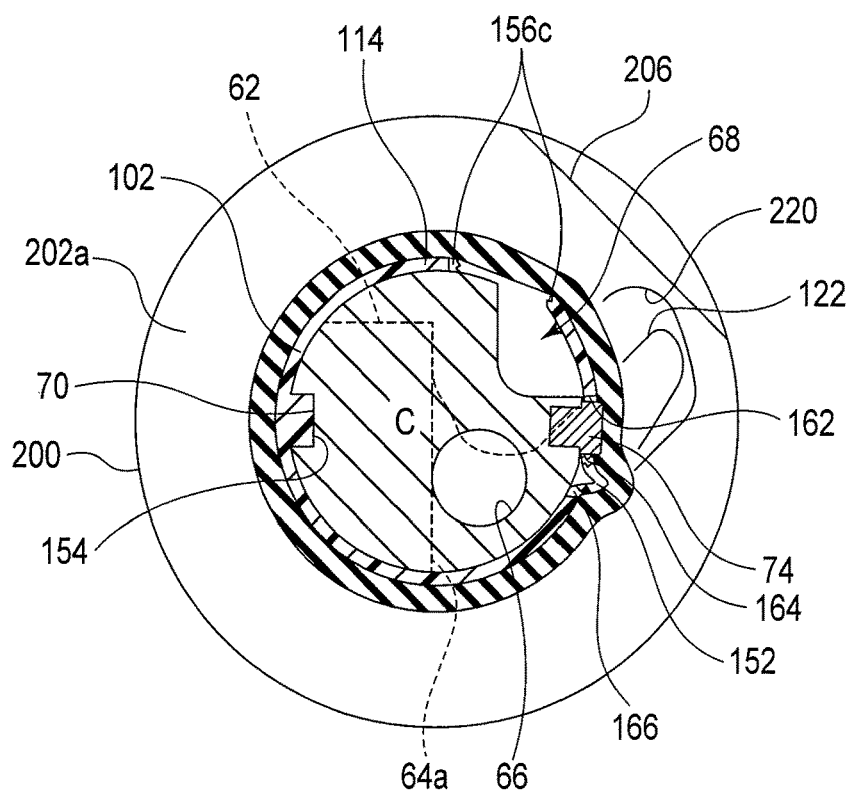
FIG. 13E is a schematic cross sectional view showing a state where the jig is twisted with respect to the cover from the state shown in FIG. 13C in a state where the jig is fitted to the cover, and the right edge of the opening edge is pressed to open the depressed portion, and a coupling portion of a fragile portion is broken.

Therefore, as shown FIG. 13C and FIG. 13E, operation force of the jig 200 is applied to the coupling portion 156c between the slits 156a and 156b of the cover 14 facing the first protruding portion 216 of the jig 200 through the pressure receiving portion 123, the right side edge 122, and the proximal side edge 130, and the coupling portion 156c is broken. Due to the breakage of the coupling portion 156c, a part including the lock depressed portion 152 of the fit portion 132 of the annular portion 114 moves in the peripheral direction while a state where the guide protruding portion 154 of the cover 14 remains fitted to the guide groove 70 of the distal framing portion 22 is maintained.

Furthermore, the lock pin 74 of the distal framing portion 22 is locked to the lock depressed portion 152 of the cover 14. In this state, if the pressure receiving portion 123 is pressed, the cover 14 turns with respective to the distal framing portion 22 around the central axis C. Accordingly, the lock depressed portion 152 moves in response to the motion of the cover 14, and presses the second fragile portion 164 toward the lock pin 74. The lock pin 74 fixed to the main body 52 of the distal framing portion 22 is higher in strength than the second fragile portion 164. Therefore, the second fragile portion 164 is broken by the lock pin 74, and the lock pin 74 is disposed in the groove 162 by the impulse of the turning of the cover 14.

Here, when stress is applied to the cover main body 102 around the central axis C in a state where the cover main body 102 is attached to the distal framing portion 22, the amount of force necessary to break the second fragile portion 164 is smaller than the amount of force which keeps the second fragile portion 164 as it is and then unlocks the lock depressed portion 152 from the lock pin 74. Thus, from the state where the lock pin 74 is locked to the lock depressed portion 152, the lock pin 74 breaks the second fragile portion 164, and is then disposed in the groove 162.

Therefore, when stress is applied to the cover 14 around the longitudinal axis L so that the fragile portion 156 is broken and the lock depressed portion (depressed lock portion) 152 is unlocked from the lock pin (first lock portion) 74 in a state where the cover 14 is attached to the distal framing portion 22, the guide protruding portion (second fit surface) 154 formed in the inner peripheral surface 102a of the cover 14 restricts movement around the longitudinal axis L with respect to the guide groove (first fit portion) 70 of the distal framing portion 22.

Thus, the lock depressed portion 152 is unlocked from the lock pin 74 in response to the breakage of the coupling portion 156c of the fragile portion 156 and in response to the breakage of the second fragile portion 164.

In addition, as shown in FIG. 13C and FIG. 13E, the right side edge 122 enters the relief portion 220 of the jig 200. If the jig 200 is further rotated with respect to the distal framing portion 22 and the cover 14 in the direction indicated by the arrow R in FIG. 12B, the user of the jig 200 needs to apply force which folds the right side edge 122 and force which breaks the depressed portions 132a and 132b by the lock pin 74. Thus, it becomes difficult for the support peripheral surface 214 of the jig 200 to slide on the turning peripheral surface 158 of the cover 14 around the central axis C. The user of the jig 200 recognizes this state. Therefore, if the jig 200 is rotated with respect to the distal framing portion 22 and the cover 14 in the direction indicated by the arrow R in FIG. 12B, the user of the jig 200 feels suitable resistibility until the coupling portion 156c of the fragile portion 156 and the second fragile portion 164 are broken and the lock pin 74 is unlocked from the lock depressed portion 152. Then the resistibility decreases, and when the lock pin 74 is disposed in the groove 162, the user again feels resistibility.

At this point, the first protruding portion 216 and the second protruding portion 218 do not touch any member of the distal framing portion 22. This prevents a load on the distal framing portion 22 when the cover 14 is detached from the distal framing portion 22 by the jig 200.

As shown in FIG. 12B, even if the jig 200 is fitted to the cover 14 in a state where the cover 14 is attached to the distal framing portion 22, the fragile portion 156 is exposed. That is, the jig 200 does not cover the fragile portion 156 and the lock depressed portion 152. Thus, for example, if the presser ring 104 is made of a transparent or semitransparent rubber material or the like, the user can directly observe a state where the fragile portion 156 and the second fragile portion 164 are broken and the lock pin 74 is disposed in the groove 162. Moreover, even if the fragile portion 156 and the second fragile portion 164 are broken by the jig 200 and the lock pin 74 is unlocked from the lock depressed portion 152, these parts are prevented from interfering with the jig 200 and interrupting the rotational breaking operation of the jig 200.

Then, as shown in FIG. 14A and FIG. 14B, the fragile portion 156 and the second fragile portion 164 are broken, and the jig 200 is pulled to the distal side along the longitudinal axis L out of the cover 14 in which the lock pin 74 is disposed in the groove 162. The fragile portion 156 and the second fragile portion 164 are broken, and the lock depressed portion 152 is unlocked from the lock pin 74 of the distal framing portion 22, so that the cover 14 is nipped by the user's fingers or a forceps or the like to remove the cover 14 to the distal side along the longitudinal axis L from the distal framing portion 22. Thus, the groove 162 is used as a guide groove for guidance when the lock pin 74 is taken out of the proximal end 114a of the annular portion 114. When the cover 14 is removed by use of the jig 200 in this way, it is possible to more easily detach the cover 14 in a state where sanitary safety of the users (surgeons and surgery staff) is ensured.

In addition, the cover 14 can come off the distal framing portion 22 together with the jig 200 depending on the state of breakage.

The detached cover (broken cover) 14 is discarded. The endoscope from the cover 14 has been detached, that is, the insertion section 12 including the distal framing portion 22, the operation section 16, and the universal cord 18 are properly washed, disinfected, and sterilized, and then reused. Further, a new cover 14 is properly attached to the distal framing portion 22, and observation and a treatment are then conducted.

Moreover, the jig 200 used to detach the cover 14 from the distal framing portion 22 may be disposed of together with the cover 14. In this case, the cover 14 and the jig 200 are preferably sold in sets as a cover unit. Additionally, the endoscope 10 including the cover 14 and the jig 200 are preferably sold in sets as an endoscope unit.

If the jig 200 is rotated with respect to the distal framing portion 22 and the cover 14 in a direction opposite to the direction indicated by the arrow R in FIG. 12B in a state where the distal framing portion 22 is held, the first protruding portion 216 of the jig 200 presses the wall surface 64a of the storage portion 64 of the main body 52 of the distal framing portion 22. Further, the counter surface 218a of the second protruding portion 218 keeps in abutment with the distal side covering portion 126a of the distal side edge 126 of the cover 14. Thus, the distal framing portion 22 and the cover 14 rotate in the same direction together with the jig 200. Therefore, the jig 200 prevents a load on the distal framing portion 22, but 115 the cover 14 can not be detached from the distal framing portion 22.

As described above, the following can be said according to the endoscope 10 in this embodiment.

The disposable type cover 14 can be used for the distal framing portion 22. Thus, the cover 14 has only to be removed at the time of the washing of the distal framing portion 22, which ensures that, for example, even the back side of the swing table 42 is easily washed by use of a brush or the like.

The fragile portion 156 composed of the slits 156a and 156b can be used to facilitate elastic deformation when the cover 14 is attached to the distal framing portion 22. Moreover, the cover 14 can be easily disposed at a predetermined rotational direction (peripheral direction) position by the guide groove 70 and the guide protruding portion 154.

When the cover 14 is detached from the distal framing portion 22, the depressed portion 124 of the open edge 116 is pressed open. At this point, the restriction portions of the distal framing portion 22 and the cover 14 (the guide groove 70 of the distal framing portion 22 and the guide protruding portion 154 of the cover 14) are made strong enough for the force in the rotational direction of the longitudinal axis L. Thus, the restriction portions keep fitted together despite the force applied in the peripheral direction of the cover 14. Therefore, the force to intensively apply stress to the fragile portion 156 of the cover 14 to detach the cover 14 can be intensively used to break the fragile portion 156 and unlock the lock portions (the lock pin 74 of the distal framing portion 22 and the lock depressed portion 152 of the cover 14). That is, the force to detach the cover 14 can be collected by the fragile portion 156. Further, the lock depressed portion 152 of the cover 14 can be unlocked from the lock pin 74 of the distal framing portion 22 by the impulse of the release of the stress resulting from the breakage of the coupling portion 156c of the fragile portion 156. It is thus possible to break the fragile portion 156 and unlock the lock portions (the lock pin 74 of the distal framing portion 22 and the lock depressed portion 152 of the cover 14) substantially at the same time.

Here, the distance of the fitting of the guide protruding portion 154 of the cover 14 to the guide groove 70 of the distal framing portion 22 is long. Thus, when the cover 14 is broken by use of the jig 200, the press force on the cover 14 can be concentrated by the breakage of the fragile portion 156 and the unlocking of the lock portions (the lock pin 74 of the distal framing portion 22 and the lock depressed portion 152 of the cover 14).

Furthermore, the fragile portion 156 can break the annular portion 114 along the longitudinal axis L, and sever the cover 14 in the peripheral direction. Therefore, the fragile portion 156 and the second fragile portion 164 are broken, the lock depressed portion 152 is unlocked from the lock pin 74, and the lock pin 74 is disposed in the groove 162, so that the cover 14 can be easily detached from the distal framing portion 22 of the insertion section 12 along the longitudinal axis L.

The fragile portion 156 and the lock depressed portion 152 are formed at positions substantially 90° to each other in the peripheral direction of the longitudinal axis L. Moreover, the distal side covering portion 126a of the cover 14 is on the distal side of the flat portion 62. This regulates the movement of the distal side covering portion 126a with respect to the right side edge 122 in the peripheral direction. Thus, if the press force is applied to open the depressed portion 124 of the open edge 116, the distal side edge 126 maintains its position, whereas the right side edge 122 moves in the peripheral direction to break the fragile portion 156, and substantially at the same time, the lock depressed portion 152 can be unlocked from the lock pin 74.

In particular, the fragile portion 156 of the cover 14 is preferably formed at a position away from the guide protruding portion 154 of the cover 14 in the peripheral direction of the central axis C, that is, at a position close to the lock depressed portion 152. Thus, the deformation amount of the fragile portion 156 can be greater than the deformation amount of the guide protruding portion 154 of the cover 14 in the peripheral direction of the central axis C. It is therefore possible to certainly break the fragile portion 156 when the cover 14 is detached from the distal framing portion 22.

Here, when the cover 14 is broken by use of the jig 200, the lock pin 74 can be disposed in the groove 162 continuous with the proximal end 114a of the cover 14, from the lock depressed portion 152 through the second fragile portion 164. Thus, when the cover 14 is detached from the distal framing portion 22, it is possible to inhibit the catching of the cover 14 and smoothly detach the cover 14 by moving the lock pin 74 along the groove 162.

By the way, the cover 14 is much smaller than the size of the user's hand. When the user detaches the cover 14 by the hand force, the movement amount of the hand is not regulated as compared to the cover 14. On the other hand, the maximum turning amount with respect to the distal framing portion 22 is regulated by use of the support peripheral surface 214 of the jig 200 and the turning peripheral surface 158 of the cover 14. Thus, when the jig 200 is used, the cover 14 can always be detached from the distal framing portion 22 by a certain operation. It is possible to prevent the user from forcibly detaching the cover 14 by the hand force by using the jig 200 when the cover 14 is detached from the distal framing portion 22.

The cover 14 attached to the distal framing portion 22 is structured so that the fragile portion 156 is not directly broken but the fragile portion 156 is indirectly broken by the jig 200 by the application of stress from a position (a position indicated by a reference number 123) away from the fragile portion 156. Moreover, when the jig 200 is used, at least a part of the fragile portion 156 is exposed. It is therefore possible to perform the breaking operation while directly visually observing the fragile portion 156.

Furthermore, when the cover 14 is detached from the distal framing portion 22 by use of the jig 200, any position of the jig 200 does not touch the distal framing portion 22 from the beginning to the end of the application of stress resulting from detachment. It is therefore possible to prevent the jig 200 from applying a load to the distal framing portion 22. That is, when the cover 14 detached from the distal framing portion 22 by the jig 200, the distal framing portion 22 is not damaged.

Therefore, to this embodiment, it is possible to provide the endoscope cover 14 which can be easily detached from the distal framing portion 22 of the insertion section 12, the endoscope 10 having this endoscope cover 14, the cover unit, and the endoscope unit.

Modifications of the first embodiment are briefly described. It should be understood that these modifications can be suitably combined.

Figure 15:
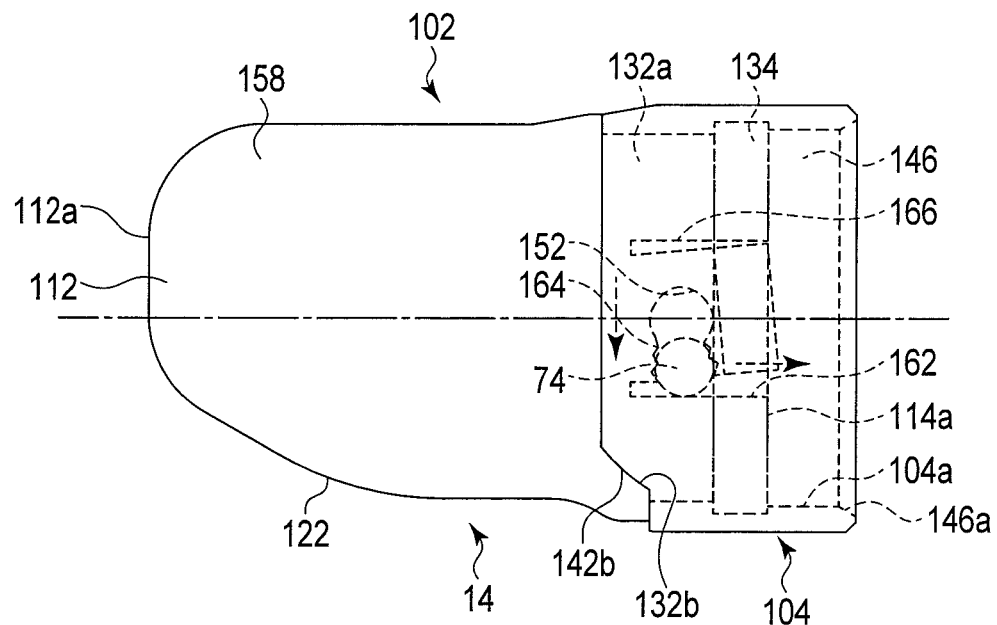
FIG. 15 is a schematic view showing a state where the second fragile portion of the cover is broken, the cover is moved to the distal side with respect to the distal framing portion along the longitudinal axis from the state where the lock pin of the distal framing portion is disposed in the groove of the cover whose width in a peripheral direction of the longitudinal axis is smaller than the diameter of the lock pin, and the lock pin, that is, the distal framing portion is pulled out along the groove, to detach the endoscope cover attached to the distal framing portion of the endoscope according to a modification (first modification) of the first embodiment.

The width of the groove 162 in the peripheral direction in the example shown in FIG. 15 is formed to be smaller than the diameter of the lock pin 74.

As shown in FIG. 15, the second fragile portion 164 is broken, and the lock pin 74 is disposed in the groove 162 from the lock depressed portion 152. At this point, a part between the groove 162 and the additional groove 166 tends to be elastically deformed due to the breakage of the second fragile portion 164. Further, the part between the groove 162 and the additional groove 166 is thus elastically deformed due to the pressure of the lock pin 74, and the lock pin 74 is pulled out of the proximal end 114a of the annular portion 114 along the groove 162.

Thus, even if the width of the groove 162 is formed to be smaller than the diameter of the lock pin 74, the groove 162 can guide the lock pin 74 when the cover 14 is pulled out of the distal framing portion 22 in the same manner as described in the first embodiment.

Figure 16A:
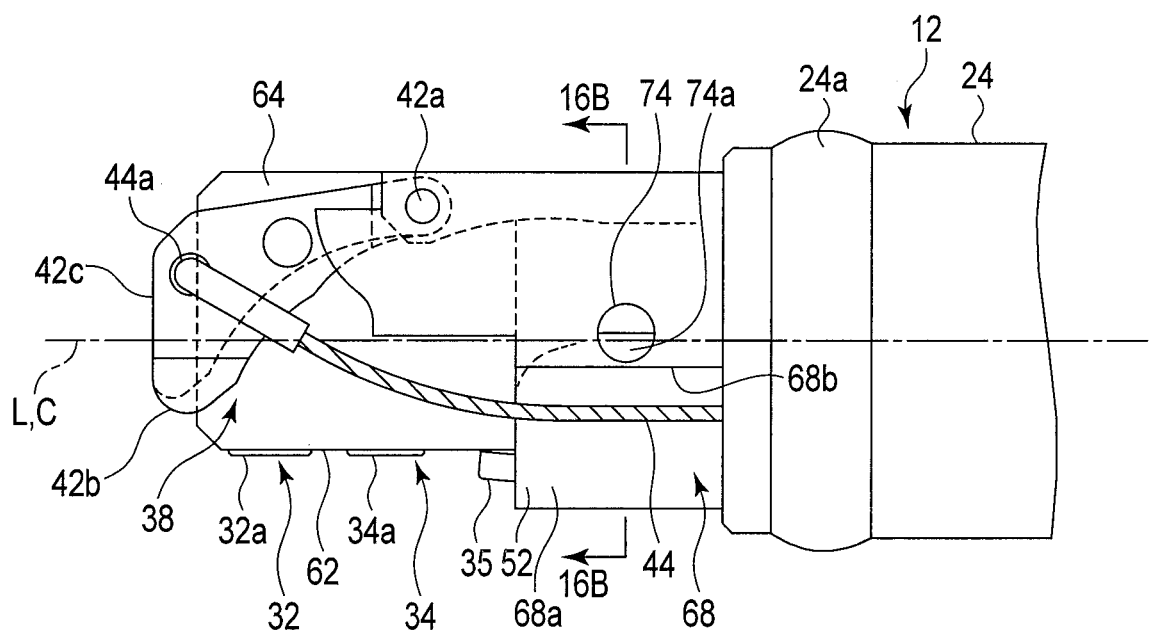
FIG. 16A is a view of the distal framing portion of the endoscope according to a modification (second modification) of the first embodiment seen from an arrow 2D side in FIG. 2B.
Figure 16B:
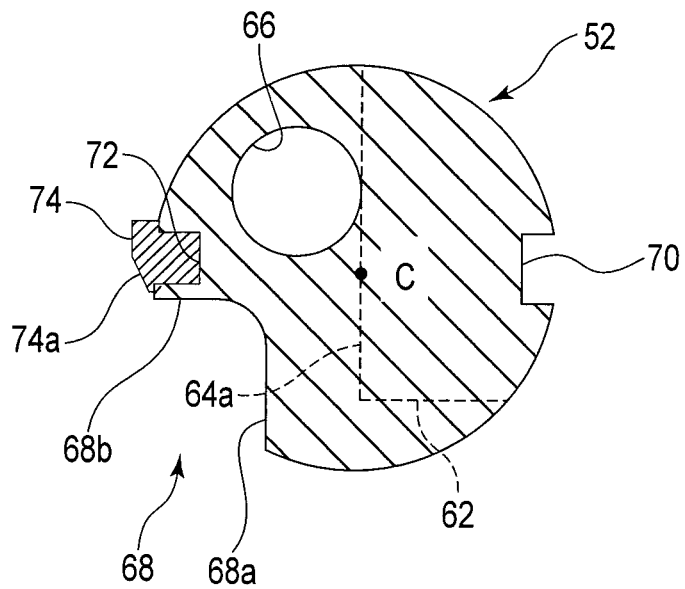
FIG. 16B is a schematic cross sectional view of the distal framing portion of the endoscope according to the modification (second modification) of the first embodiment, taken along the line 16B-16B in FIG. 16A.
Figure 16C:
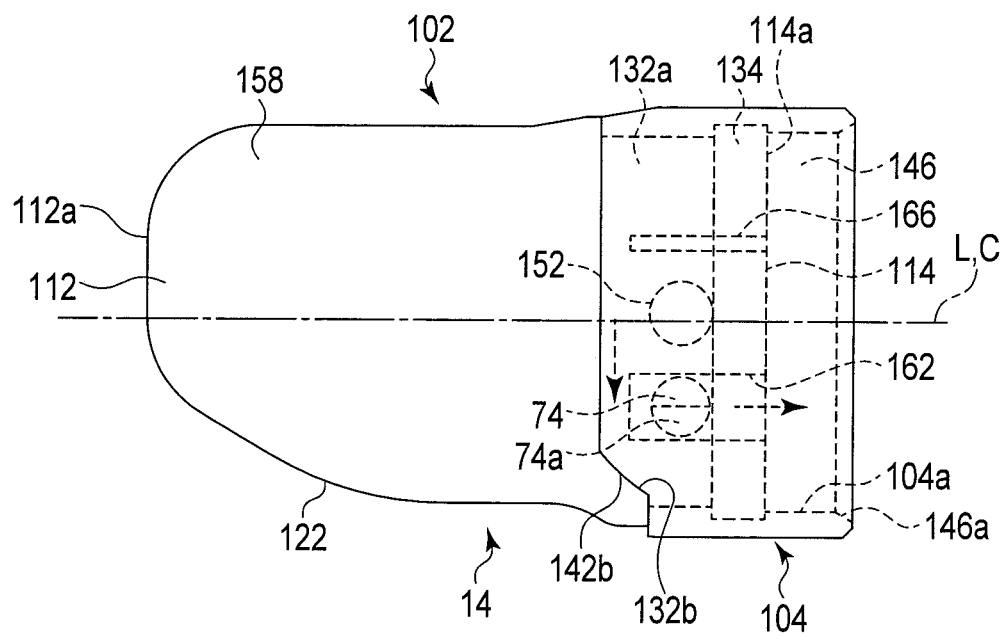
FIG. 16C is a schematic view showing a state where the lock pin of the distal framing portion is disposed in the groove without breaking a part between a lock depressed portion and the groove adjacent to the lock depressed portion from the state where the lock pin is locked to the lock depressed portion, the cover is moved to the distal side with respect to the distal framing portion along the longitudinal axis, and the lock pin, that is, the distal framing portion is pulled out along the groove, to detach the endoscope cover attached to the distal framing portion of the endoscope according to the modification (second modification) of the first embodiment.

In the example shown in FIG. 16A to FIG. 16C, the lock pin 74 has an inclined plane 74a. The inclined plane 74a is smaller in protrusion amount on the side close to the wire moving portion 68 with respect to the central axis C, and increases in protrusion amount as it comes away from the wire moving portion 68.

In a state where the cover 14 is attached to the distal framing portion 22, the inclined plane 74*a* is formed on the side close to the groove 162 rather than the additional groove 166. Thus, when the lock depressed portion 152 is unlocked from the lock pin 74, the lock depressed portion 152 slides along the inclined plane 74*a* by the impulse of this unlocking, due to the presence of the inclined plane 74*a*. Therefore, the lock depressed portion 152 is easily unlocked from the lock pin 74 owing to the inclined plane 74*a*.

Furthermore, as shown in FIG. 16C, here, the second fragile portion 164 (see FIG. 4C and FIG. 5C) is not present between the lock depressed portion 152 and the groove 162. Even in such a case, when the lock depressed portion 152 is unlocked from the lock pin 74, the lock depressed portion 152 slides along the inclined plane 74*a* by the impulse of this unlocking. Thus, the lock pin 74 is easily disposed in the groove 162.

Figure 17:
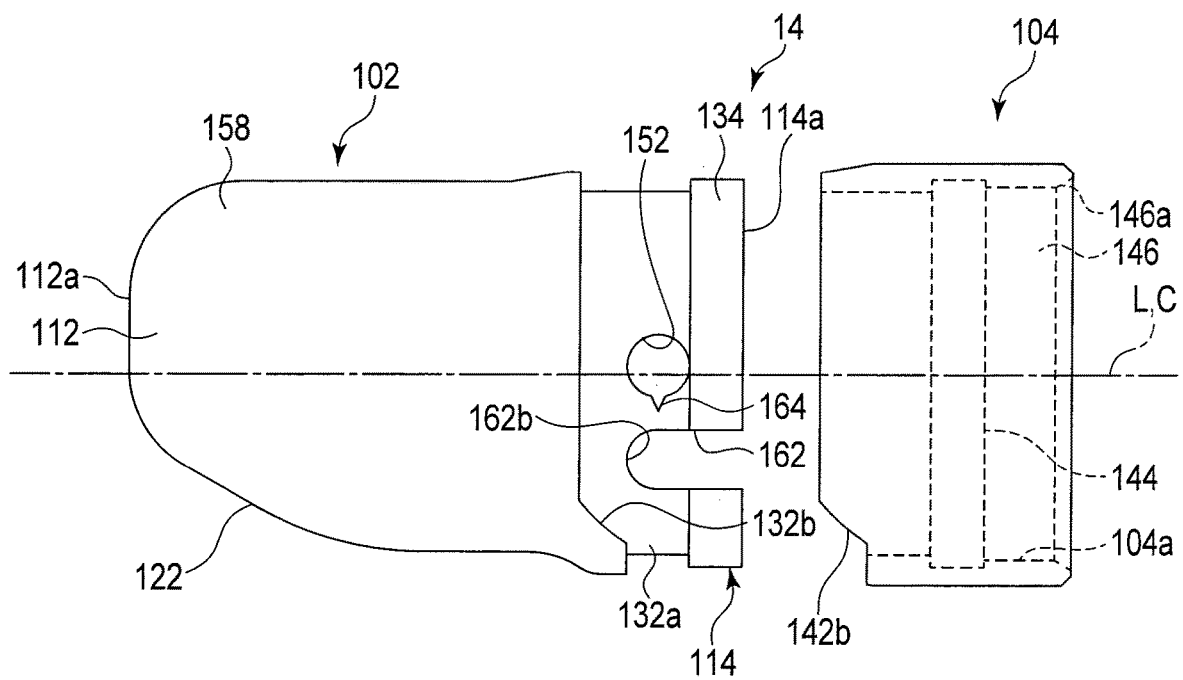
FIG. 17 is a view of a state seen from the arrow 4C side in FIG. 4A where the endoscope cover which is attached to the distal framing portion of the endoscope according to a modification (third modification) of the first embodiment is exploded.

In the example shown in FIG. 17, the distal end of the groove 162 is not formed into a state having the corner portion 162*a*, but is formed as a semicircular edge 162*b*. Moreover, the additional groove 166 does not necessarily need to be formed. This also applies to the examples described below.

Figure 18:
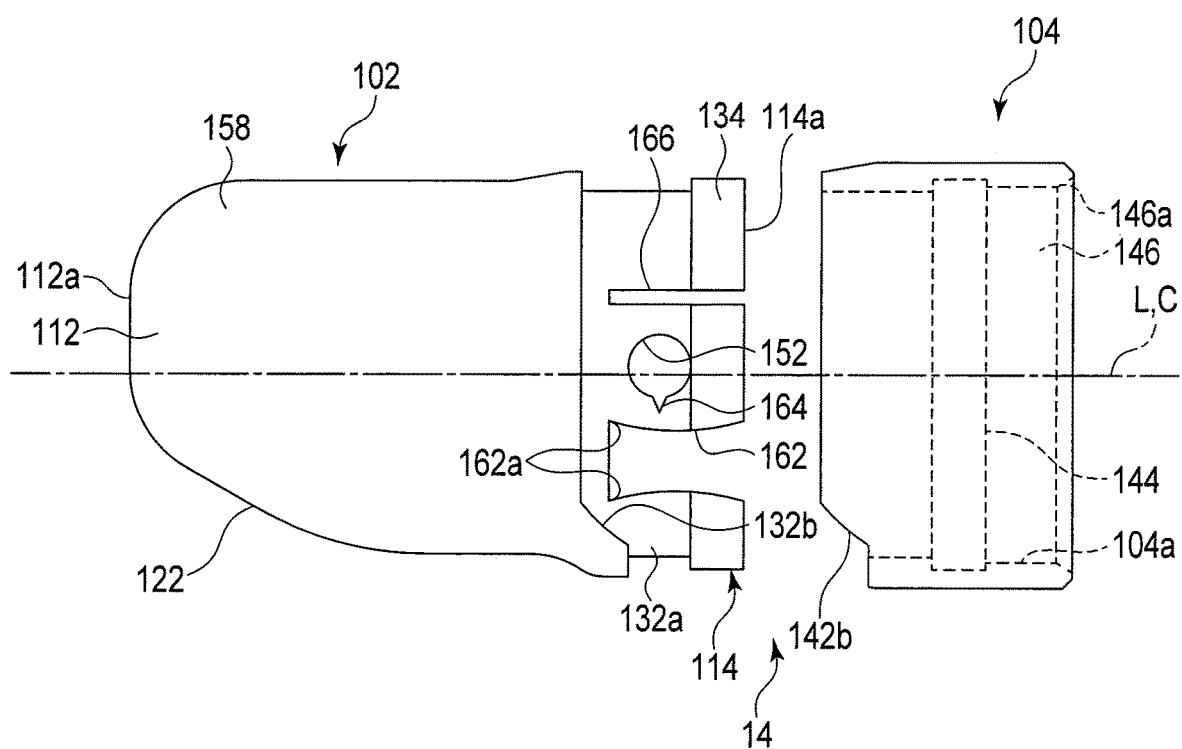
FIG. 18 is a view of a state seen from the arrow 4C side in FIG. 4A where the endoscope cover which is attached to the distal framing portion of the endoscope according to a modification (fourth modification) of the first embodiment is exploded.

In the example shown in FIG. 18, the groove 162 is not formed parallel from its distal end toward its proximal end, but is formed as an edge of a curved surface. As shown in FIG. 18, the width of the groove 162 is maximized at the position of the corner portion 162*a* of the distal end and at the position of the proximal end. It is appropriate that the vicinity of the distal end and the vicinity of the proximal end of the groove 162 be formed to be the same as or slightly larger than the diameter of the lock pin 74. At least a part between the distal end and the proximal end of the groove 162 may be formed to be slightly smaller than the diameter of the lock pin 74. When the cover 14 is moved with respect to the distal framing portion 22 along the central axis C in a state where the lock pin 74 is disposed in the groove 162, the part between the groove 162 and the additional groove 166 can be elastically deformed.

Figure 19:
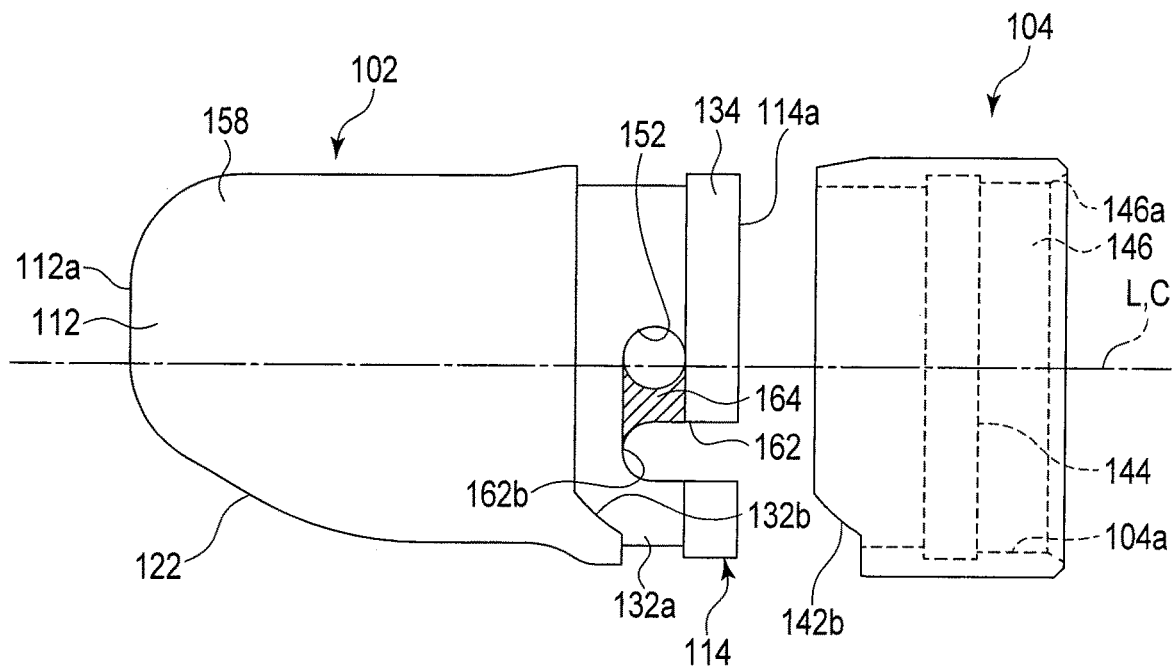
FIG. 19 is a view of a state seen from the arrow 4C side in FIG. 4A where the endoscope cover which is attached to the distal framing portion of the endoscope according to a modification (fifth modification) of the first embodiment is exploded.

In the example shown in FIG. 19, the second fragile portion 164 is not formed as the slit (see FIG. 4C) but formed as a thin portion thinner than the other adjacent parts (periphery). The second fragile portion 164 functions in the same manner as the slit even when the second fragile portion 164 is not the slit but the thin portion. As the second fragile portion 164, the inner peripheral surface 102*a* of the annular depressed portion 132*a* may be formed into a depressed shape, or the outer peripheral surface of the depressed portion 132*a* may be formed into a depressed shape.

Figure 20A:
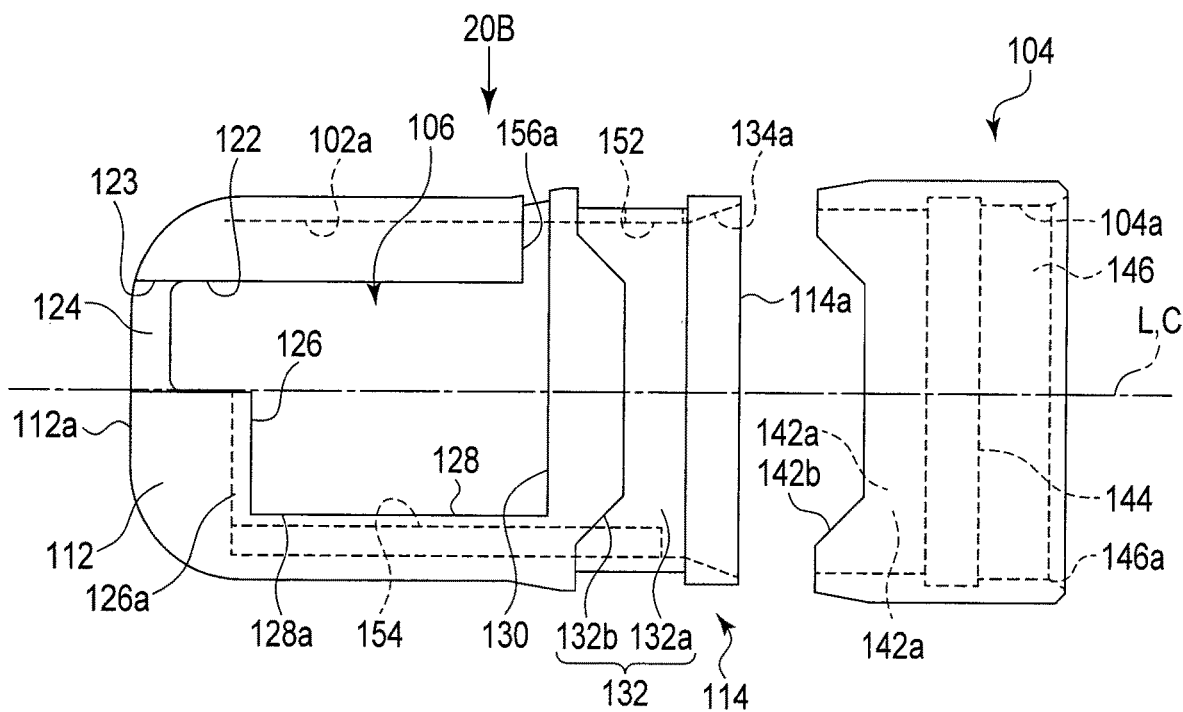
FIG. 20A is a schematic view showing a state where the endoscope cover which is attached to the distal framing portion of the endoscope according to a modification (sixth modification) of the first embodiment is exploded.
Figure 20B:
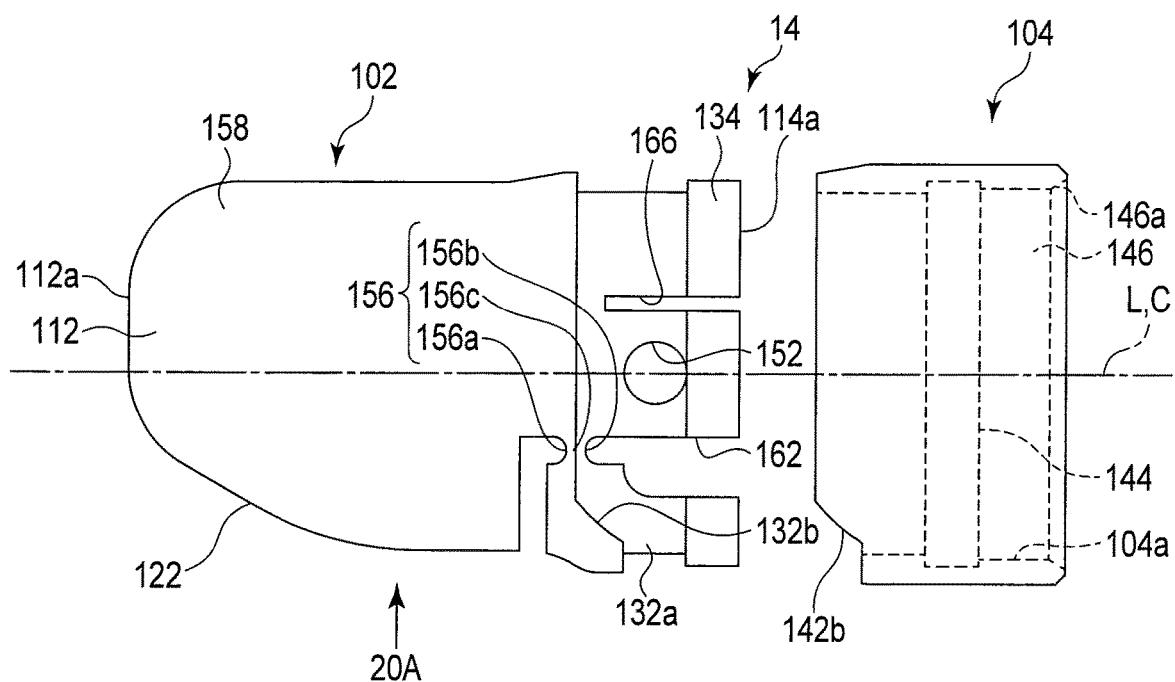
FIG. 20B is a view of a state seen from, an arrow 20B side in FIG. 20A where the endoscope cover which is attached to the distal framing portion of the endoscope according to the modification (sixth modification) of the first embodiment is exploded.

In the example shown in FIG. 20A and FIG. 20B, the fragile portion 156 and the groove 162 are continuously formed. Here, the slit 156*a* is formed in the peripheral direct on from the proximal end of the right side edge 122. The slit 156*b* is continuous with the groove 162. Even when the cover main body 102 is formed as above, the cover 14 shown in FIG. 20A and FIG. 20B can be used in the same manner as the cover 14 described in the first embodiment (see FIG. 4A to FIG. 5C).

Now, the second embodiment is described with reference to FIG. 21A to FIG. 24B. This embodiment is a modification of the first embodiment including its modifications described above, and the same reference numbers are given to the same components as the components described in the first embodiment or to the components having the same functions, and detailed explanations are omitted.

Figure 21A:
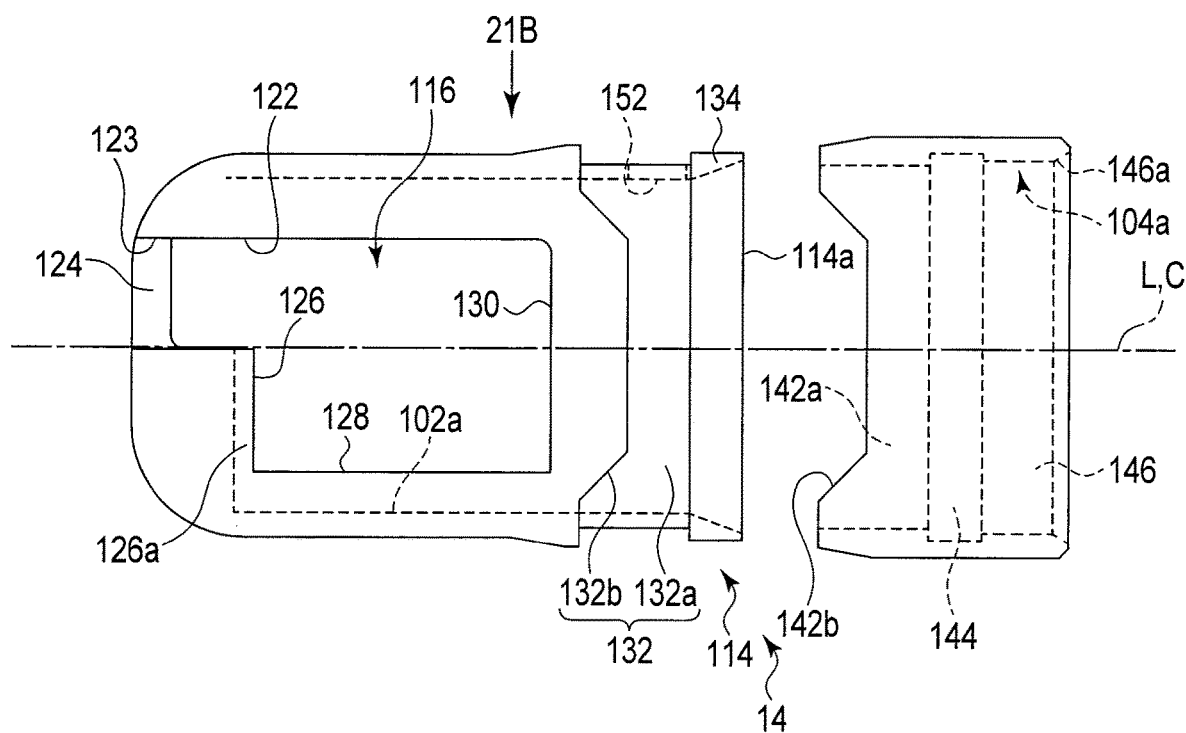
FIG. 21A is a schematic view showing a state where the endoscope cover which is attached to the distal framing portion of the endoscope according to the second embodiment is exploded.
Figure 21B:
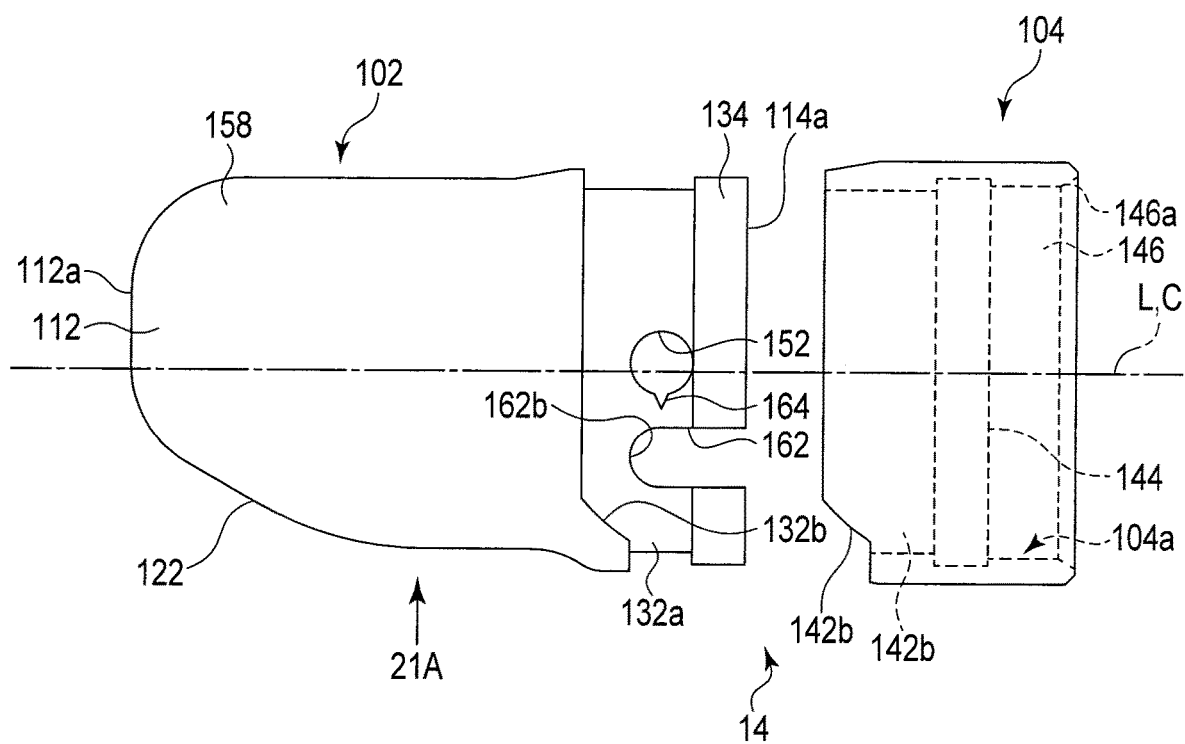
FIG. 21B is a view of a state seen from an arrow 21B side in FIG. 21A where the endoscope cover which is attached to the distal framing portion of the endoscope according to the second embodiment is exploded.
Figure 22:
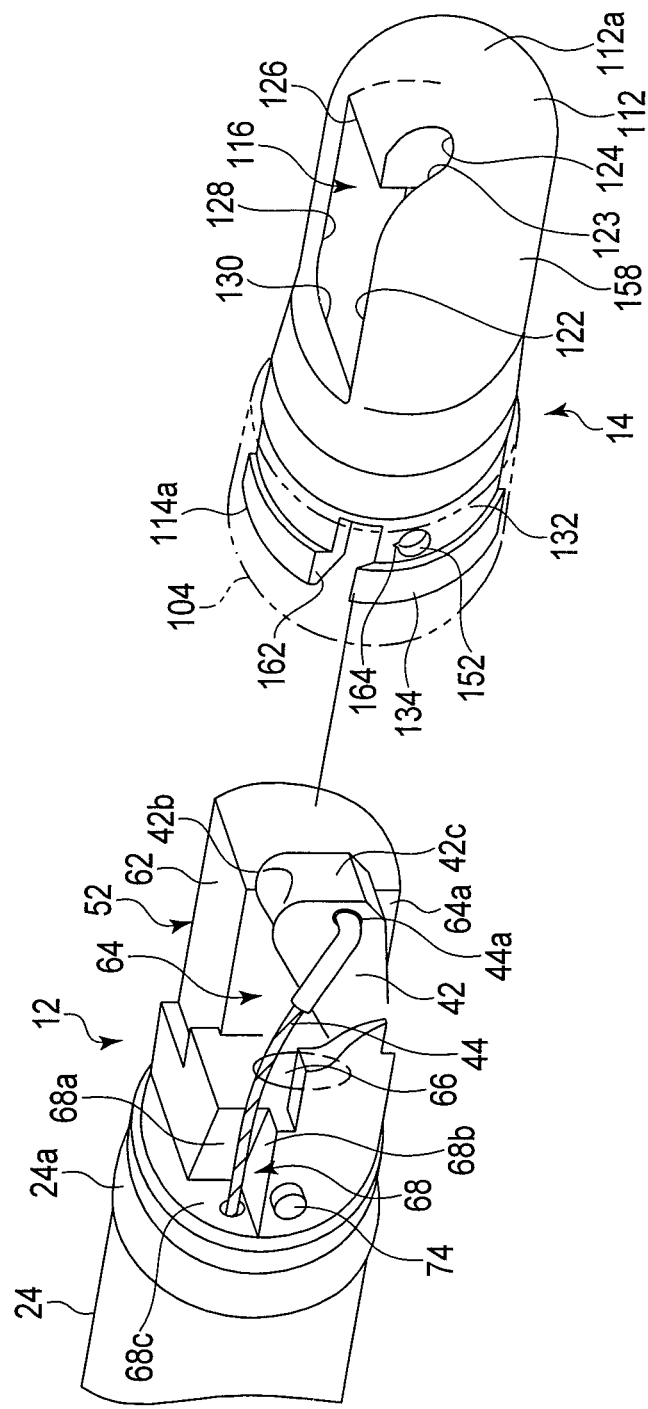
FIG. 22 is a schematic perspective view showing a state where the endoscope cover is to be attached to the distal framing portion of the endoscope according to the second embodiment.

In the examples described in the first embodiment, the cover 14 has the fragile portion 156. As shown in FIGS. 21A and 22, the fragile portion 156 is not necessarily needed. Moreover, in the examples described in the first embodiment, the guide groove 70 is formed in the main body 52 of the distal framing portion 22, the guide protruding portion 154 is formed in the inner peripheral surface 102*a* of the cover 14, and the guide protruding portion 154 is fitted to the guide groove 70. As shown in FIG. 22, the guide groove 70 of the distal framing portion 22, and the guide protruding portion 154 of the inner peripheral surface 102*a* of the cover 14 are not necessarily needed. Further, as shown in FIG. 21B, the additional groove 166 is not necessarily needed either.

Here, the distal end of the groove 162 is not formed into a state having the corner portion 162*a*, but is formed as the semicircular edge 162*b*. In addition, the groove 162 is permitted to have a suitable shape described in the modifications of the first embodiment.

As shown in FIG. 22 and FIG. 23A, the orientation of the cover 14 in the peripheral direction of the longitudinal axis L is defined with respect to the distal framing portion 22, and the cover 14 is then attached to the distal framing portion 22. When the cover 14 is attached to the distal framing portion 22, the skirt portion 146*a* of the fit portion 146 of the presser ring 104 of the cover 14 abuts on the lock pin 74 of the distal framing portion 22. At this point, the fit portion 146 is elastically deformed due to its elasticity. Thus, the lock pin 74 of the distal framing portion 22 abuts on the skirt portion 134*a* of the annular portion 114 of the cover main body 102. At this point, the annular portion 114 is elastically deformed by the groove 162. Thus, the lock depressed portion 152 is locked to the lock pin 74 of the distal framing portion 22. Therefore, the lock pin 74 and the lock depressed portion 152 define the positions of the cover 14 with respect to the distal framing portion 22 in the peripheral direction and the axial direction, and prevent the displacement of the cover 14 with respect to the distal framing portion 22 in the peripheral direction and the axial direction.

After the use of the endoscope 10, the cover 14 is detached from the distal framing portion 22. When the cover 14 is detached from the distal framing portion 22, the cover 14 is turned with respect to the distal framing portion 22 around the central axis C by use of force of the user's fingers, and the lock pin 74 of the distal framing portion 22 is disposed in the groove 162. After the lock depressed portion 152 is unlocked from the lock pin 74 as above, it is not impossible to move the cover 14 to the distal side with respect to the central axis C and then detach the cover 14. However, when the cover 14 is detached from the distal framing portion 22 by the user's fingers, the way of detachment can differ from user to user. There is therefore concern that it may become difficult to stably break the second fragile portion 164.

It is therefore preferable that, the cover 14 according to this embodiment is also detached from the distal framing portion 22 by use of the jig 200 described in the first embodiment.

Figure 24A:
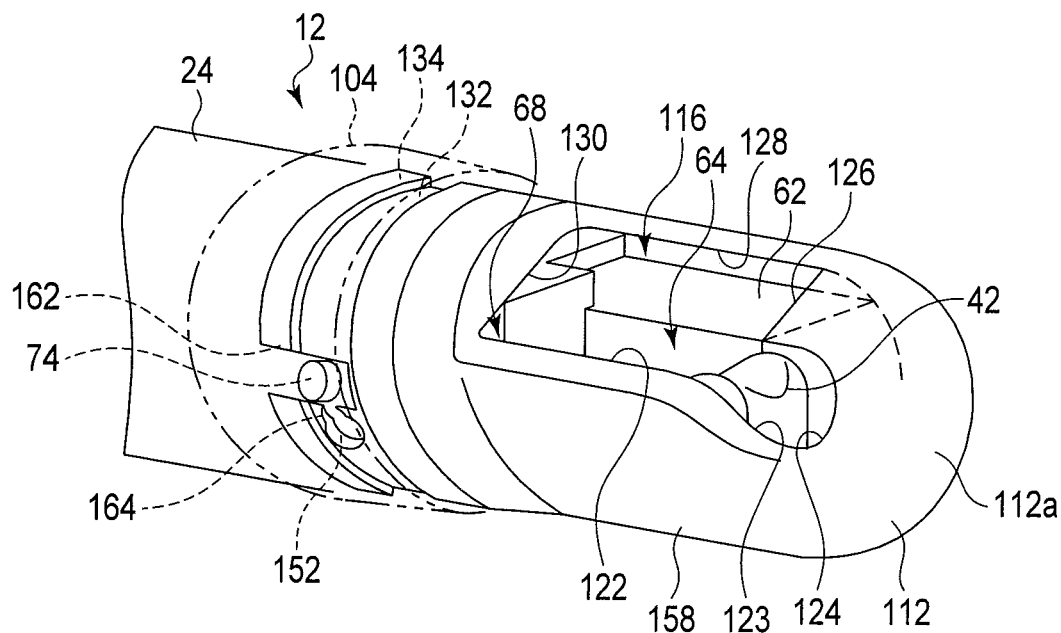
FIG. 24A is a schematic perspective view showing a state where the cover is twisted with respect to the distal framing portion, the fragile portion between the lock depressed portion of the cover and the groove is broken, and the lock pin of the distal framing portion is disposed in the groove of the cover to detach the endoscope cover attached to the distal framing portion of the endoscope according to the second embodiment.
Figure 24B:
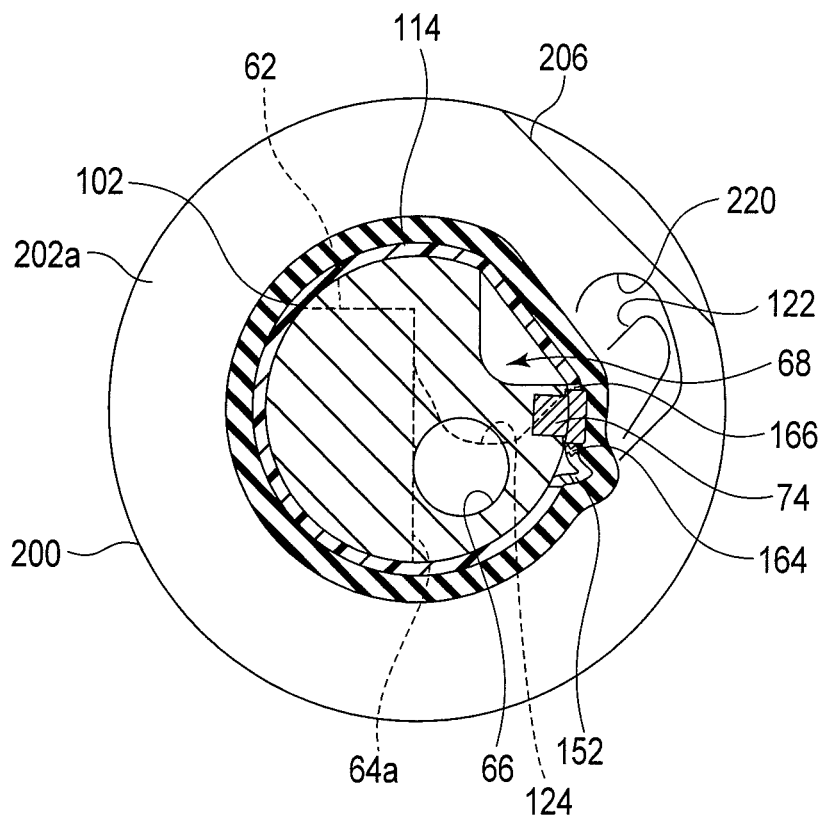
FIG. 24B is a schematic cross sectional view taken along the line 13C-13C in FIG. 13A, showing a state where the jig is twisted with respect to the cover in a state where the jig is fitted to the cover, the right edge of the opening edge is then pressed to open a depressed portion, and the fragile portion between the lock depressed portion of the cover and the groove is broken, to detach the endoscope cover attached to the distal framing portion of the endoscope according to the second embodiment.

As shown in FIG. 23B and FIG. 24B, the operation force amount of the jig 200 is applied to the lock depressed portion 152 of the cover 14 through the pressure receiving portion 123 and the right side edge 122 of the cover 14. At this point, the guide groove 70 (see FIG. 2A and FIG. 6) of the distal framing portion 22 and the guide protruding portion 154 of the cover 14 (see FIG. 6) are not present. However, because the part of the bending portion 24 on the distalmost possible side is held by the user, turning of the distal framing portion 22 around the central axis C is prevented. Therefore, in the same manner as described in the first embodiment, the distal framing portion 22 does not turn and the cover 14 alone turns even when the jig 200 is used. Consequently, as shown in FIG. 24A and FIG. 24B, from the state where the lock pin 74 is locked to the lock depressed portion 152, the lock pin 174 breaks the second fragile portion 164, and is then disposed in the groove 162.

Here, when stress is applied to the cover main body 102 around the central axis C in a state where the cover main body 102 is attached to the distal framing portion 22, the amount of force necessary to break the second fragile portion 164 is smaller than the amount of force which keeps the second fragile portion 164 as it is and then unlocks the lock depressed portion 152 from the lock pin 74. Thus, from the state where the lock pin 74 is locked to the lock depressed portion 152, the lock pin 74 breaks the second fragile portion 164, and is then disposed in the groove 162.

Then, as shown in FIG. 24A, the second fragile portion 164 is broken, and the jig 200 is pulled to the distal side along the longitudinal axis L from the cover 14 in which the lock pin 74 is disposed in the groove 162.

Thus, even if the fragile portion 156 is not formed in the cover 14, the cover 14 can be attached to the distal framing portion 22, and the cover 14 can be properly detached from the distal framing portion 22.

Modifications of the second embodiment are briefly described below. It should be understood that these modifications can be suitably combined.

The appearance in the example shown in FIG. 25 is the same as that in the example shown in FIG. 18. However, the guide protruding portion 154 is not formed in the inner peripheral surface 102a of the cover main body 102.

Figure 26A:
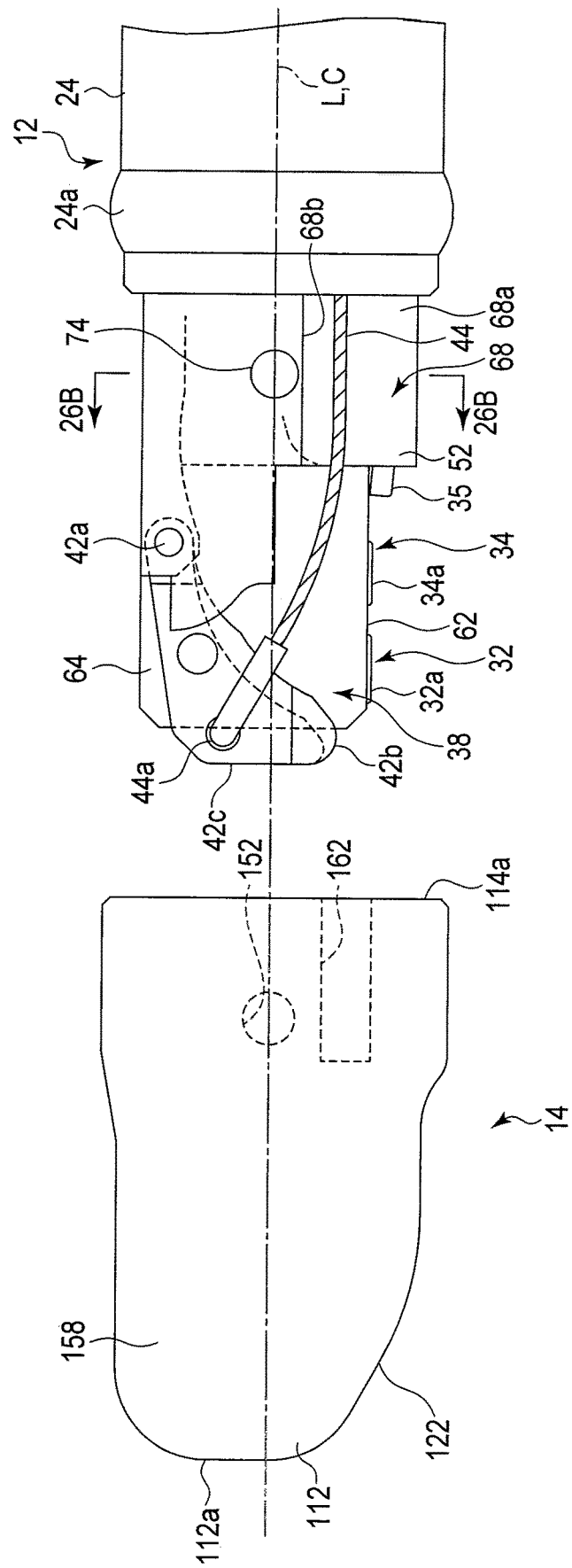
FIG. 26A is a diagram of the endoscope cover which is attached to the distal framing portion of the endoscope according to a modification (second modification) of the second embodiment seen from the arrow 21B side in FIG. 21A, and distal framing portion seen from the arrow 2D side in FIG. 2B.

In the example shown in FIG. 26A, the cover main body 102 and the presser ring 104 are integrated. That is, in the example shown in FIG. 26A, the presser ring 104 which is separate from the cover main body 102 and which is made of the rubber material is not used. Here, the fragile portions 156 and 164 are not formed. The groove 162 is not shown in the outer periphery of the cover 14, and is formed in the inner peripheral surface. Thus, the part of the cover 14 in which the groove 162 is formed is thinner than other adjacent parts.

Figure 26B:
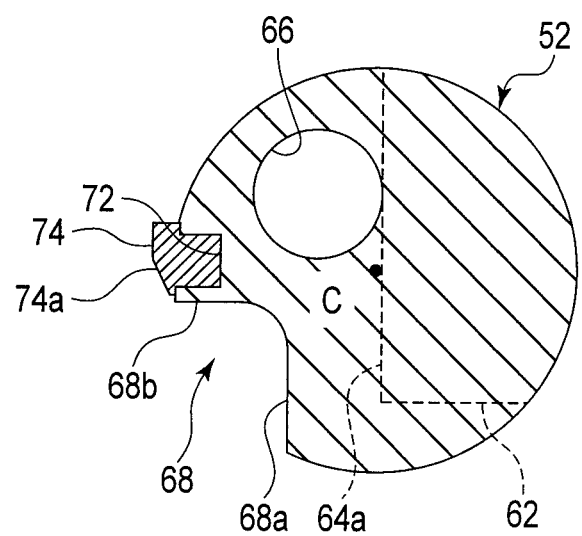
FIG. 26B is a schematic cross sectional view of the distal framing portion of the endoscope according to the modification (second modification) of the second embodiment, taken along the line 26B-26B FIG. 26A.

Furthermore, as shown in FIG. 26A and FIG. 26B, the lock pin 74 has the inclined plane 74a as in the example shown in FIG. 16A to FIG. 16C. In a state where the cover 14 is attached to the distal framing portion 22, the inclined plane 74a is at a position close to the groove 162. Thus, when the lock depressed portion 152 is unlocked from the lock pin 74, the lock depressed portion 152 slides along the inclined plane 74a by the impulse of this unlocking, due to the presence of the inclined plane 74a. Therefore, the lock depressed portion 152 is easily unlocked from the lock pin 74 owing to the inclined plane 74a.

Furthermore, as shown in FIG. 26A, here, the second fragile portion 164 (see FIG. 4C and FIG. 5C) is not present between the lock depressed portion 152 and the groove 162. Even in such a case, when the lock depressed portion 152 is unlocked from the lock pin 74, the lock depressed portion 152 slides along the inclined plane 74a by the impulse of this unlocking. Thus, the lock pin 74 is easily disposed in the groove 162.

In addition, the guide protruding portion 154 may be formed in the inner peripheral surface 102a of the cover main body 102. That is, the example in which the cover main body 102 and the presser ring 104 are integrated can naturally be used instead of the cover 14 described in the first embodiment.

In the first and second embodiments described above, the normal N (see FIG. 2C, FIG. 3B, and FIG. 3C) to the flat portion 62 in which the illumination window 32a and the observation window 34a are provided is formed to be in the direction substantially orthogonal to the longitudinal axis L. However, the direction of the normal N to the flat portion 62 can be suitably set. In this case, the shape of the active portion 204 of the jig 200 has only to be suitably formed.

Although the distal framing portion 22 is the side-viewing type in the examples according to the first and second embodiments described above, the distal framing portion 22 may naturally be formed as a so-called direct-viewing type to observe in the direction along the longitudinal axis L of the insertion section 12, or a so-called oblique-viewing type to observe in a suitable direction between the direction along the longitudinal axis L of the insertion section 12 and the direction orthogonal to the longitudinal axis L.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope cover configured to be attached in a lock state to a convex-shaped protruding lock portion of a distal framing portion of an insertion section of an endoscope, the endoscope cover comprising:
    a cylindrical cover main body including a ring-shaped annular portion, the cover main body being attached to the distal framing portion along a longitudinal axis of the insertion section;
    a concave-shaped depressed lock portion provided on the cover main body, the depressed lock portion being configured to lock to the protruding lock portion of the distal framing portion;
    a first groove provided on a part including a proximal end of the annular portion of the cover main body along the longitudinal axis, the first groove being provided adjacent to the depressed lock portion in a peripheral direction of the longitudinal axis and in which the protruding lock portion is configured to be located when the cover main body is turned with respect to the distal framing portion in the peripheral direction of the longitudinal axis and then the protruding lock portion is unlocked from the depressed lock portion; and
    a second groove provided on a part including the proximal end of the annular portion of the cover main body along the longitudinal axis and which elastically deforms the depressed lock portion when the protruding lock portion is locked to the depressed lock portion.

2. The endoscope cover according to claim 1, wherein the width of the first groove along the peripheral direction of the longitudinal axis is formed to be equal to or more than the width of the protruding lock portion of the distal framing portion along the peripheral direction of the longitudinal axis.

3. The endoscope cover according to claim 1, wherein the depressed lock portion is between the first groove and the second groove.

4. The endoscope cover according to claim 1, further comprising a fragile portion provided between the depressed lock portion and the first groove, the fragile portion being configured to be deformed or broken when the protruding lock portion moves from the depressed lock portion to the first groove.

5. The endoscope cover according to claim 4, wherein the fragile portion has at least one of a slit and a thin portion thinner than other parts between the depressed lock portion and the first groove.

6. The endoscope cover according to claim 1, further comprising a fragile portion at least partly provided on the annular portion of the cover main body, the fragile portion being configured to be broken by the application of stress to the annular portion.

7. An endoscope comprising:
the endoscope cover according to claim 1;
the distal framing portion configured to be inserted into a lumen and which includes a protruding lock portion that diametrically outwardly protrudes with regard to a longitudinal axis of the insertion section; and
the endoscope cover, in which the depressed lock portion is locked to the protruding lock portion when the endoscope cover is attached to the distal framing portion along the longitudinal axis.

8. The endoscope according to claim 7, wherein
the distal framing portion includes a part of a swing mechanism configured to swing a treatment instrument at the distal end of the insertion section, and
the cover main body of the endoscope cover includes an open edge configured to expose a swing table of the swing mechanism to the outside.

9. An endoscope unit comprising:
the endoscope according to claim 7; and
a jig configured to detach the endoscope cover from the distal framing portion when the endoscope cover is attached to the distal framing portion.

10. A cover unit comprising:
the endoscope cover according to claim 1; and
a jig configured to detach the endoscope cover from the distal framing portion from a state where the endoscope cover is attached to the distal framing portion.

11. The cover unit according to claim 10, wherein:
the cover main body of the endoscope cover includes an open edge configured to expose a swing table of a swing mechanism of the distal framing portion to the outside, and
in the state where the endoscope cover is attached to the distal framing portion, the jig is configured to apply a stress to the open edge of the cover main body around the longitudinal axis, and unlock the depressed lock portion from the protruding lock portion of the distal framing portion.

12. The endoscope cover according to claim 1, wherein:
the annular portion is provided on a proximal end of the cover main body, and
the first groove is provided along the longitudinal axis.

13. The endoscope cover according to claim 1, further comprising a presser cover configured to cover at least a part of the cover main body,
wherein the presser cover covers the annular portion.

14. The endoscope cover according to claim 1, wherein the second groove is provided along the longitudinal axis.

* * * * *